(12) United States Patent
Nido et al.

(10) Patent No.: US 12,171,859 B2
(45) Date of Patent: Dec. 24, 2024

(54) TOPICAL COMPOSITION AND METHOD OF USE

(71) Applicant: ALLERGAN SALES, LLC, North Chicago, IL (US)

(72) Inventors: Patrick Nido, Brea, CA (US); Kuniko Kadoya, San Diego, CA (US); Prithwiraj Maitra, Ladera Ranch, CA (US); Rahul Mehta, San Marcos, CA (US); Elizabeth Makino, Carlsbad, CA (US)

(73) Assignee: ALLERGAN SALES, LLC, North Chicago, IL (US)

(*) Notice: Subject to any disclaimer, the term of this patent is extended or adjusted under 35 U.S.C. 154(b) by 37 days.

(21) Appl. No.: 17/824,425

(22) Filed: May 25, 2022

(65) Prior Publication Data

US 2022/0387284 A1 Dec. 8, 2022

Related U.S. Application Data

(60) Provisional application No. 63/192,771, filed on May 25, 2021, provisional application No. 63/251,247, filed on Oct. 1, 2021.

(51) Int. Cl.
| | |
|---|---|
| *A61K 8/64* | (2006.01) |
| *A61K 8/81* | (2006.01) |
| *A61K 8/89* | (2006.01) |
| *A61K 8/9728* | (2017.01) |
| *A61K 8/9783* | (2017.01) |
| *A61Q 19/06* | (2006.01) |

(52) U.S. Cl.
CPC .............. *A61K 8/64* (2013.01); *A61K 8/8147* (2013.01); *A61K 8/89* (2013.01); *A61K 8/9728* (2017.08); *A61K 8/9783* (2017.08); *A61Q 19/06* (2013.01)

(58) Field of Classification Search
CPC ........ A61Q 19/06; A61K 8/64; A61K 8/9728; A61K 8/9783; A61K 8/8147; A61K 8/89
See application file for complete search history.

(56) References Cited

U.S. PATENT DOCUMENTS

| | | | |
|---|---|---|---|
| 9,408,881 B2 | 8/2016 | Gruber et al. | |
| 10,286,030 B2 | 5/2019 | Garruto et al. | |
| 2004/0132667 A1* | 7/2004 | Lintner | A61K 38/07 514/1.1 |
| 2010/0197805 A1* | 8/2010 | Cassin | A61K 8/31 514/772.1 |
| 2012/0076842 A1 | 3/2012 | Fournial et al. | |
| 2014/0309173 A1* | 10/2014 | Dreher | A61K 9/0019 548/339.1 |
| 2015/0202139 A1 | 7/2015 | Friedman | |
| 2018/0255834 A1* | 9/2018 | Dillmann | A24B 15/167 |

FOREIGN PATENT DOCUMENTS

WO 2007078056 7/2007

OTHER PUBLICATIONS

Makino et al., "Clinical Efficacy of a Novel Topical Treatment for Neck Rejuvenation: A Randomized, Double-Blind, Regimen-Controlled Study," Abstract presented at Maui Derm Winter Clinical Dermatology Conference, Maui, Hawaii Jan. 15-20, 2021 and Orlando Dermatology Aesthetic Conference, Orlando, Florida Jan. 15-18, 2021.
Makino et al., "Clinical Efficacy of a Novel Topical Treatment for Neck Rejuvenation: A Randomized, Double-Blind, Regimen-Controlled Study," Poster presented at Maui Derm Winter Clinical Dermatology Conference, Maui, Hawaii Jan. 15-20, 2021 and Orlando Dermatology Aesthetic Conference, Orlando, Florida Jan. 15-18, 2021.
Cescon et al., "Collagen VI at a Glance," J Cell Sci., Oct. 2015; 128, pp. 3525-3531.
Koga et al., "Protein Homeostasis and Aging: The Importance of Exquisite Quality Control," Ageing Res Rev., Apr. 2011; 10, pp. 205-215.
Rohrich et al., "Neck Rejuvenation Revisited," Plast Reconstr Surg., Oct. 2006; 118, pp. 1251-1263.
Tsukahara et al., "Selective Inhibition of Skin Fibroblast Elastase Elicits a Concentration-Dependent Prevention of Ultraviolet B-Induced Wrinkle Formation," J Invest Dermatol., Sep. 2001; 117, pp. 671-677.
Perez, "An Anatomic Approach to the Rejuvenation of the Neck," Dermatol Clin., Apr. 2001; 19(2), pp. 387-396.
Vanaman et al., "Neck Rejuvenation Using a Combination Approach: Our Experience and a Review of the Literature," Dermatol Surg., May 2016; 42 Suppl 2, pp S94-S100.
Skinmedica Essential Defense Mineral Shield SPF 35 product information; https://www.skinmedica.com/us/skin-concern/sun-protection/95703.html, accessed Aug. 22, 2022.
Skinmedica Facial Cleanser product information; https://www.skinmedica.com/us/product-category/facial-cleansers/94944.html, accessed Aug. 22, 2022.
Makino, et al., "Clinical Efficacy of a Novel Topical Treatment for Neck Rejuvenation: A Randomized, Double-Blind, Regimen-Controlled Study," Poster Presentation at a virtual conference of the American Academy of Dermatology, Apr. 23-25, 2021.
Makino, et al., "Efficacy and Tolerability of a Novel Topical Treatment for the Neck: A Randomized, Double-Blind, Regimen-Controlled Study," Journal of Drugs in Dermatology, vol. 20(2), Feb. 2021, pp. 184-191.
Makino et al., "Efficacy of Firm & Tone Body Lotion For Upper Arms in a Double-Blind, Randomized, Vehicle-Controlled Clinical Study," Abstract presented at the American Society for Dermatologic Surgery, Chicago, Illinois Oct. 14-17, 2021 and the Fall Clinical Dermatology Conference, Las Vegas, Nevada Oct. 21-24, 2021.
Makino et al., "Efficacy of Firm & Tone Body Lotion For Upper Arms in a Double-Blind, Randomized, Vehicle-Controlled Clinical Study," Poster presented at the Fall Clinical Dermatology Conference, Las Vegas, Nevada Oct. 21-24, 2021.

(Continued)

*Primary Examiner* — Blessing M Fubara

(74) *Attorney, Agent, or Firm* — FLOREK & ENDRES PLLC

(57) ABSTRACT

The present invention relates to a topical composition that can be used to treat skin laxity, cellulite and to firm, smooth and/or tone skin.

20 Claims, 16 Drawing Sheets

(56) References Cited

OTHER PUBLICATIONS

Makino et al., "Efficacy of Firm & Tone Body Lotion For Upper Arms in a Double-Blind, Randomized, Vehicle-Controlled Clinical Study," Slides From Oral Presentation presented at the American Society for Dermatologic Surgery, Chicago, Illinois Oct. 14-17, 2021.

Makino et al., "Efficacy of Firm & Tone Body Lotion For Thighs in a Double-Blind, Randomized, Vehicle-Controlled Clinical Study," Abstract presented at the American Society for Dermatologic Surgery, Chicago, Illinois Oct. 14-17, 2021 and the Fall Clinical Dermatology Conference, Las Vegas, Nevada Oct. 21-24, 2021.

Makino et al., "Efficacy of Firm & Tone Body Lotion For Thighs in a Double-Blind, Randomized, Vehicle-Controlled Clinical Study," Poster presented at the Fall Clinical Dermatology Conference, Las Vegas, Nevada Oct. 21-24, 2021.

Makino et al., "Efficacy of Firm & Tone Body Lotion For Thighs in a Double-Blind, Randomized, Vehicle-Controlled Clinical Study," Slides From Oral Presentation presented at at the American Society for Dermatologic Surgery, Chicago, Illinois Oct. 14-17, 2021.

Cestari TF, et al., "Acquired Hyperpigmentations," Anais brasileiros de dermatologia. Jan. 2014;89:11-25.

López-Otín C, et al., "The Hallmarks of Aging," Cell. Jun. 6, 2013;153(6):1194-217.

* cited by examiner

TOPICAL COMPOSITION AND METHOD OF USE

CROSS-REFERENCE TO RELATED APPLICATIONS

This application claims the benefits of U.S. Provisional Application Ser. No. 63/192,771, filed on May 25, 2021 and U.S. Provisional Application Ser. No. 63/251,247, filed on Oct. 1, 2021, the disclosures of which are incorporated herein by reference in their entirety.

FIELD OF THE INVENTION

The present invention relates to topical compositions and methods for skincare treatment employing the topical compositions disclosed herein. More specifically, the topical compositions and methods for skincare disclosed herein are cosmetic compositions or formulations, particularly body toning and firming cosmetic compositions or formulations. The topical compositions may be applied to various areas of human skin, such as a submental region, abdomen, face, neck, flank, back, chest, arm, leg, buttocks or combination thereof.

BACKGROUND

When skin ages naturally or prematurely, it thins and gradually loses its firmness, wrinkles and/or sags. This can be explained by the fact that the elastic fibers of the dermal extracellular matrix, forming the support and conferring elasticity and strength to the skin are destroyed and become rare with age.

Skin laxity or loose skin is part of the natural aging process. Skin laxity may also occur due to environmental factors such as exposure to UV rays, pollutants and smoking. Skin laxity may also be a temporary result of energy-based fat reduction methods and other treatments targeting deeper fatty tissues.

There is a need for an easy to use topical composition that can improve skin laxity, tighten, tone, smooth and/or firm skin and/or reduce cellulite.

SUMMARY OF THE INVENTION

The present invention is a topical composition that may be applied to various skin areas of a human subject, such as a submental region, abdomen, face, neck, flank, back, chest, arm, leg, buttocks or combination thereof. The topical composition comprises a tripeptide, a tetrapeptide or a combination thereof. In certain embodiments, the topical composition may further comprise one or more botanical extracts that are extracellular matrix ("ECM") agents; cellular recycling ("CR") agents; adipose targeting ("AT") agents; antioxidants or combinations thereof.

In certain embodiments, the topical composition comprises about 0.0001 wt % to about 2.00 wt % based on the total weight of the composition of a tripeptide, about 0.0001 wt % to about 2.00 wt % based on the total weight of the composition of a tetrapeptide or a combination thereof.

In certain embodiments, the topical composition will comprise about 0.0001 wt % to about 5 wt % based on the total weight of the composition of one or more botanical extracts wherein the one or more botanical extracts comprise one or more ECM agents; one or more CR agents; or combinations of the foregoing.

In certain embodiments, the topical composition will comprise about 0.0001 wt % to about 10 wt % based on the total weight of the composition of one or more botanical extracts wherein the one or more botanical extracts comprise one or more AT agents.

In certain embodiments, the topical composition will comprise about 0.0001 wt % to about 5 wt % based on the total weight of the composition of one or more antioxidants and in certain embodiments the one or more antioxidants will comprise at least one antioxidant that is a botanical extract.

The topical composition may be a solution, suspension, dispersion, emulsion, gel, cream, lotion, ointment or serum and further comprise conventional topical/cosmetic carriers, auxiliaries or excipients such as one or more thickeners/viscosity enhancing agents, film forming polymers, emollients, chelating agents, humectants, preservatives, pH adjusting agents, buffering agents, solvents, surfactants, emulsifiers, sunscreen agents and combinations of the foregoing.

The topical composition may be applied to various skin areas of a human subject, such as a submental region, abdomen, face, neck, flank, back, chest, arm, leg, buttocks or combination thereof at least once, twice, thrice or more times a day. In certain embodiments, the topical composition is applied to various skin areas of a human subject, such as a submental region, abdomen, face, neck, flank, back, chest, arm, leg, buttocks or combination thereof, that was also the target of a body shaping procedure such as a high frequency focused ultrasound procedure, a pulsed focus ultrasound procedure, a cryolipolysis procedure, a radiofrequency induced electroporation procedure, an injectable lipolytic agent procedure, a liposuction procedure, or combinations thereof.

DETAILED DESCRIPTION OF THE DRAWINGS

DETAILED DESCRIPTION OF THE INVENTION

Figure 1A:
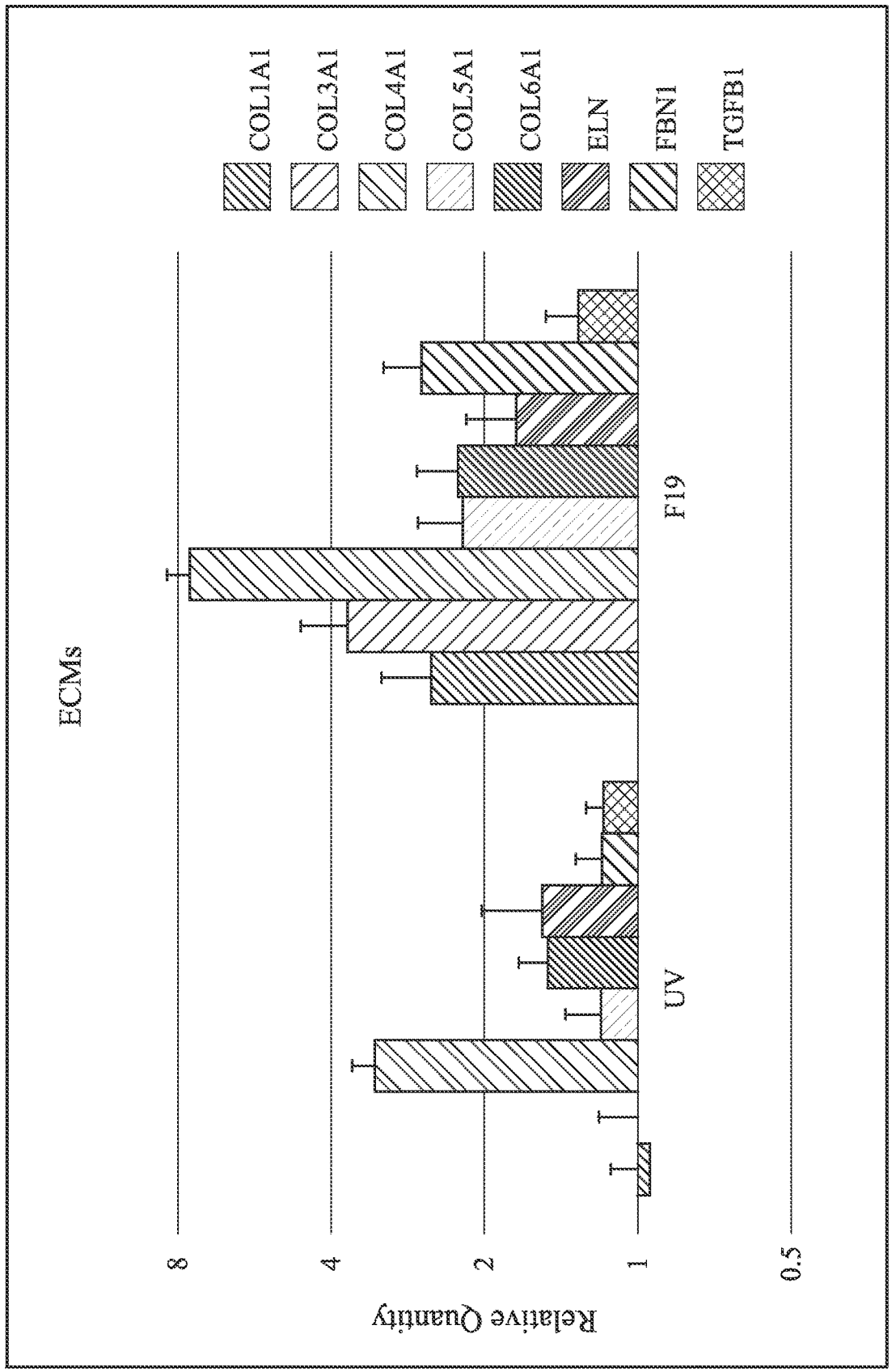
FIGS. 1A-1E show the results of the in vitro tests described in Example 3.

Before the present invention is further described, it is to be understood that this invention is not limited to the particular embodiments described. It is also to be understood that the terminology used herein is for the purpose of describing particular embodiments only, and is not intended to be limiting.

It should be noted that as used herein, the singular forms "a," "an," and "the" include plural referents unless the context clearly dictates otherwise.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used herein, the terms "extracellular matrix agent" or "ECM agent" refers to a compound, preferably a botanical extract that has a composition similar to the main components of the skin dermis and/or dermal epidermal junction ("DEJ") such as collagens, elastin and laminins. The ECM agents may increase ECM synthesis and/or inhibit ECM enzymes such as collagenases and elastases that catalyze the degradation or breakdown of collagen and elastin fibers. The ECM agent may also reduce carbamylation that in turn prevents or deters the deterioration of collagen and other ECM proteins and thereby improves the organization of collagen.

As used herein, the terms "cellular recycling agent" or "CR agent" refers to a compound, preferably a botanical extract that induces or promotes collagen recycling. For example, the CR agent may promote Endo180, an endocytic recycling glycoprotein expressed on fibroblasts that induces the collagen sustainability cycle, such as autophagy. The CR agent may also induce or maintain proteasome activity. For example, the CR agent may help maintain or increase ubiquitin-proteasome ("Ub-P") levels and aid in decreasing senescence markers.

As used herein, the terms "adipose targeting agent" or "AT agent" refers to a compound, preferably a botanical extract that exhibits an anti-adipogenic effect such as inhibiting adipocyte differentiation, reducing localized fat by induction of lipolysis, reducing fat by reducing lipogenesis, improving the quality of blood vessels and lymphatic vessels to facilitate removal of fatty acids and discharge excess tissue liquids. The AT agent may also reduce the amount of cellulite and/or improve the appearance of cellulite in a targeted area. The pathophysiology of cellulite is complex and involves the presence of excess subcutaneous fat, the microcirculatory system, lymphatics, inflammation, and the extracellular matrix. Cellulite is a condition of adipose tissue wherein the balance between lipolysis and lipogenesis is impaired. This imbalance is believed to have hormonal or nutritional origins. When this imbalance occurs, adipose cells grow excessively (i.e. up to 100 times their original size) by accumulating lipids. In parallel, their ability to capture sugars is amplified. The sugar excess results in a rigidifying of collagen fibers which normally provide elasticity to skin. Adipocytes saturated with lipids become trapped in this network of rigid fibers. Lymphatic vessels become unable to properly reach inside this tissue which in turn results in water retention and inadequate toxin elimination. Over time fatty deposits pockets are generated that form characteristic dimples and bumps on the affected areas (orange-peel like appearance).

As used herein the term antioxidant broadly refers to a compound that retards oxidation or degradation. The antioxidant may retard the oxidation or degradation of one or more ingredients in the topical composition and/or may retard the oxidation or degradation of the components of the skin cells in the target area or application site. Unless specifically stated, the antioxidant may be a commonly known antioxidant such as those described in the United State Pharmacopeia or Handbook of Pharmaceutical Excipients, a botanical extract or a combination thereof.

Unless defined otherwise, all technical and scientific terms used herein have the same meaning as commonly understood by one of ordinary skill in the art to which this invention belongs. For example, as used herein the following nomenclature maybe employed to refer to various amino acids forming the peptides useful in the present invention: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present invention is a topical composition that may be applied to a human subject's outer skin surface such as a submental region, abdomen, face, neck, flank, back, chest, arm, leg, buttocks or combination thereof.

The topical compositions in accordance with the present invention may be a solution, suspension, dispersion, emulsion, gel, cream, lotion, ointment or serum. In certain embodiments, the topical composition is a gel, cream, lotion, ointment or serum. Embodiments of the topical compositions may exhibit a viscosity of less than 100,000 cps, preferably less than 75,000 cps and more preferably less than 50,000 cps at 25° C. when tested using a conventional viscosity apparatus, such as a Brookfield RVT viscometer with spindle 2 and 20 rpms. In certain embodiments, the topical composition will exhibit a viscosity at 25° C. between about 3,000 cps and 75,000 cps, preferably about 5,000 cps and about 60,000 cps and more preferably about 7,000 cps and about 50,000 cps.

The topical compositions in accordance with the present invention should also exhibit a pH of about 5 to about 8, preferably about 5.5 to about 7.5 and more preferably about 6 to about 7. The pH may be controlled using buffer solutions or other pH modifying agents. Examples of pH modifying agents include but are not limited to, phosphoric acid and/or phosphate salts, citric acid and/or citrate salts, hydroxide salts (i.e., calcium hydroxide, sodium hydroxide, potassium hydroxide) and amines, such as triethanolamine. Examples of buffers include, acetic acid and salts, citric acid and salts, boric acid and salts, and phosphoric acid and salts such as mono- and dipotassium phosphate, citric acid/sodium citrate, and dibasic sodium phosphate/citric acid.

The topical compositions in accordance with the present invention may comprise one or more tripeptides. In certain embodiments, the topical compositions will comprise about 0.0001 wt % to about 2.00 wt %, preferably about 0.0002 wt % to about 1.00 wt % and more preferably about 0.0003 wt % to about 0.5 wt % of the total weight of the topical composition of one or more tripeptides. The tripeptide should reduce progerin production in the skin cells. Progerin is a protein that causes nuclear defects and can increase DNA damage. Examples of tripeptides that may be used in the compositions are described in U.S. Pat. No. 10,286,030 and U.S. Patent Application Publication No. 2012/0076842, which are incorporated herein by reference. Additional examples, include but are not limited to, palmitoyl tripeptide-1 (commercially available under the tradename (MATRIXYL 3000), palmitoyl tripeptide-5 (commercially available under the tradename SYN-COLL), copper tripeptide-1 (commercially available under the tradename TEGO PEP3-RECOVER), palmitoyl tripeptide-28 (commercially available under the tradename ECM MODULINE PEPTIDE POWDER), tripeptide-1 (commercially available under the tradename (KOLLAREN) and trifluoroacetyl tripeptide-2 (commercially available under the tradename PROGELINE). In certain embodiments, the tripeptide may be functionalized with known chemical moieties such as a fatty acid to improve the properties of the tripeptide such as to enhance the skin permeation or penetration. In certain embodiments, the preferred tripeptide comprises Val-Try-Val amino acid sequence.

The topical compositions in accordance with the present invention may comprise one or more tetrapeptides. In certain embodiments, the topical composition will comprise about 0.0001 wt % to about 2.00 wt %, preferably about 0.0002 wt % to about 1.00 wt % and more preferably about 0.0003 wt % to about 0.5 wt % of the total weight of the topical composition of one or more tetrapeptides. The tetrapeptide should enhance the natural elements that maintain collagen levels and elastin fiber assembly. The tetrapeptide may also induce the elastic fiber proteins, elastin and fibrilli-1 protein synthesis, assist in the synthesis of other proteins for elastic fiber assemblies such as fubulin5 and LOXL-1 and may assist with production of focal adhesion molecules such as talin and zyxin. Examples of tetrapeptides that may be used in the topical compositions are described in U.S. Pat. No. 10,286,030 and U.S. Patent Application Publication No. 2012/0076842, which are incorporated herein by reference. Additional examples include but are not limited to palmitoyl tetrapeptide-7 (commercially available under the tradenames MATRIXYL 3000 or HALOXYL), tetrapeptide-30 (commercially available under the tradename TEGO PEP 4-EVEN), palmitoyl tetrapeptide-72 (commercially available under the tradename SKINARCH) and acetyl tetrapeptide-2 (commercially available under the tradename UPLEVITY). In certain embodiments, the tetrapeptide may be functionalized with known chemical moieties such as fatty acids to improve the properties of the tetrapeptide such as to enhance the skin permeation or penetration. In certain embodiments, the preferred tetrapeptide comprises Lys-Asp-Val-Try amino acid sequence.

Although other peptides may also optionally be present in the topical compositions of the present invention such as dipeptides, pentapeptide, hexapeptides and heptapeptides which are also described in U.S. Pat. Nos. 10,286,030; 10,493,011 and U.S. Patent Application Publication No. 2012/0076842, in certain embodiments of the present invention, the topical compositions are free, (i.e., 0 wt % or below detectable limits) or substantially free, (i.e., less than 0.00005 or 0.00001 wt %) of peptides other than the one or more tripeptides, one or more tetrapeptides or a combination thereof.

The topical compositions in accordance with the present invention may comprise one or more ECM agents, preferably one or more botanical ECM agents. In certain embodiments, the topical compositions will comprise about 0.001 wt % to about 2.50 wt %, preferably about 0.005 wt % to about 1.50 wt % and more preferably about 0.007 wt % to about 1.00 wt % based on the total weight of the topical composition of one or more ECM agents. Examples of ECM agents that may be used in the present invention include, but are not limited to, *Chlorella vulgaris* extract as described in International Patent Application No. WO 2007/078056 and commercially available under the tradename CHLORELLAGEN, and mushroom extracts such as *Lentinus edodes* extract, commercially available under the tradename ACTIFICOL.

The topical compositions in accordance with the present invention may comprise one or more CR agents, preferably one or more botanical CR agents. In certain embodiments, the composition will comprise about 0.0005 wt % to about 2.50 wt %, preferably about 0.001 wt % to about 1.50 wt % and more preferably about 0.0025 wt % to about 1.00 wt % based on the total weight of the topical composition of one or more CR agents. Examples of CR agents that may be used in the present invention include but are not limited to *Melissa officinalis* leaf extract, aka lemon balm, commercially available under the tradename RECYCOLL 180 and rice extracts such a hydrolyzed rice protein, commercially available under the tradename PROLIXIR-ICE.

The topical compositions in accordance with the present invention may comprise one or more AT agents, preferably one or more botanical AT agents. In certain embodiments, the composition will comprise about 0.001 wt % to about 10.00 wt %, preferably about 0.01 wt % to about 7.50 wt % and more preferably about 0.05 wt % to about 5.00 wt % based on the total weight of the topical composition of one or more AT agents. Examples of AT agents that may be used in the present invention include, but is not limited to plant extracts (i.e. fruit, vegetable, leguminous, flower, and/or spice extracts), algae extracts, microorganisms extracts such as yeast extracts and their derivatives, ferments, proteolytic hydrolysates, peptides, animal derivative extracts and synthetic compounds. More particularly, specific examples of AT agents that may be used in the topical compositions of the present invention include: *Oenanthe javanica* extract, commercially available under the tradename ISONARI; a mixture of *Coffea arabica* (coffee) seed oil and *Brassica campestris* (rapeseed) sterols, commercially available under the tradename SLIMBUSTER L 3R); a mixture of caffeine, *coleus* forskohilii root extract, and *Chlorella vulgaris/Lupines albus* protein ferment, commercially available under the tradename CELLACTIVE SHAPE); a mixture of cocoglucoside, caprylyl glycol and glaucine, commercially available under the tradename BODYLIFT; a mixture of hydrolyzed *Celosia cristata* flower seed extract and hydrolized prunella vulgaris extract, commercially available under the tradename BIOSCULPTINE; *Nelumbo nucifera* leaf extract, commercially available under the tradename PRO-SV-ELTYL; *Citrus aurantium amara* (bitter orange) flower extract, commercially available under the tradename REMODULINE; *Peumus boldus* leaf extract, commercially available under the tradename SLIMACTIVE; *Cecrpia obtusa* extract, commercially available under the tradename SLIM FIT; caffeine; theobromine; yohimbine; carnitine; *Asiatica cantella*; rutin; *Celosia cristata* extract; prunella vulgaris extract; hesperetin laurate; *Imperata cylindrica* extract; licorice extract; *Coffea arabica* (coffee) seed oil; *Brassica campestris* (rapeseed) sterols, *Coleus forskohilii* root extract, *Chlorella vulgaris/Lupines albus* protein ferment and combinations thereof. Additional AT agents are described in U.S. Patent Application Publication Nos. 2011/1058922; 2011/0268688; 2017/0014334; and 2020/0297654 which are incorporated herein by reference. A method for determining the potential AT activity of a compound is described in U.S. Patent Application Publication No. 2003/086949, which is incorporated herein by reference.

The topical compositions in accordance with the present invention may comprise one or more antioxidants. In certain embodiments, the topical composition will comprise about 0.0005 wt % to about 5.00 wt %, preferably about 0.0007 wt % to about 4.0 wt % and more preferably about 0.001 wt % to about 3.00 wt % based on the total weight of the topical composition of one or more antioxidants. Examples of antioxidants that can be used with the topical compositions of the present invention include, but are not limited to, acetyl cysteine, ascorbic acid polypeptide, ascorbyl dipalmitate, ascorbyl methylsilanol pectinate, ascorbyl palmitate, ascorbyl stearate, butylated hydroxyanisole (BHA), butylated hydroxytoluene (BHT), t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, *Helianthus annus* (sunflower) seed oil, hydroquinone, isooctyl thioglycolate, kojic acid, *Laminaria digitata* extract, magnesium ascorbate, magnesium ascorbyl phosphate, methylsilanol ascorbate, natural botanical anti-oxidants such as *Camellia sinnensis* green tea extract or vitris vimfera (grape) callous culture extract, nordihydroguaiaretic acid, octyl gallate, phenylthioglycolic acid, potassium ascorbyl tocopheryl phosphate, potassium sulfite, propyl gallate, quinones, rosmarinic acid, rosa mochata seed oil, *Rosmarinus officinalis* (rosemary) leaf extract, sodium ascorbyl phosphate, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, tremella fuciformis (mushroom) extract, tris(nonylphenyl)phosphite, and *Zea mays* (corn) oil. In certain embodiments, the topical compositions comprise one or more antioxidants that are botanical extracts such as, *Zingiber officinate* (ginger) root extract, commercially available under the tradename SYMVITAL AGE REPAIR and combinations thereof. In certain embodiments, the topical compositions may also comprise one or more non-botanical extract antioxidants such as tocopherol, propyl gallate, hydroxyacetaphenone.

In certain embodiments, the topical composition of the present invention may comprise one or more antioxidants that also impart anti-inflammatory properties to the target area where the topical composition is applied. Examples of compounds that impart antioxidant and anti-inflammatory properties include but are not limited to resorcinols, extracts and materials derived from the following: *Phellodendron amurense* corte extract (PCE), *Tanacetum parthenium* commercially available under the tradename FEVERFEW, *Zingiber officinate* (ginger) root extract, ginko (*Ginkgo biloba*), *Centella asiatica* extract, commercially available under the tradename MADECASSOSIDE, cotinus (*Cotinus coggygria*), butterbur extract (*Petasites hybridus*), goji berry (*Lycium barbarum*), milk thistle extract (*Silybum marianum*), honeysuckle (*Lonicera japonica*), basalm of peru (*Myroxylon pereirae*), sage (*Salvia officinalis*), cranberry extract (*Vaccinium oxycoccos*), amaranth oil (*Amaranthus cruentus*), pomegranate (*Punica granatum*), yerbe mate (*Ilex paraguariensis* leaf extract), white lily flower extract (*Lilium candidum*), olive leaf extract (*Olea europaea*), phloretin (apple extract), oat flour (*Aveena sativa*), hops (*Humulus lupulus*) extract, commercially available under the tradename LIFENOL, bugrane p (*Ononis spinosa*), licochalcone (licorice: *Glycyrrhiza inflate* extract ingredient), bisabolol and ginger extract, commercially available under the tradename SYMRELIEF, and combinations thereof. Additional examples may be found in U.S. Patent Application Publication Nos. 2020/0069562 and 2017/0128357, which are incorporated herein by reference.

The topical compositions of the present invention may be a solution, suspension, dispersion, emulsion, gel, cream, lotion, ointment or serum and further comprise conventional topical/cosmetic carriers, auxiliaries and/or excipients. The CTFA International Cosmetic Ingredient Dictionary and Handbook (2008), 12$^{th}$ Edition, describes a wide variety of non-limiting cosmetic ingredients that may be used in embodiments of the present invention. Examples of these ingredient classes include but are not limited to fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, essential oils, vitamins (e.g., A, B, C, D, E, and K), trace metals (e.g., zinc, calcium and selenium), anti-irritants (e.g., steroids and non-steroidal anti-inflammatories), anti-microbial agents, chelating agents (e.g., disodium EDTA, tetrasodium EDTA, and phytic acid), preservatives (e.g., benzalkonium chloride, benzyl alcohol, phenol, urea, thimerosal, chlorobutanol, paraben such as methylparaben, propylparaben, phenoxyethanol, sodium benzoate, and potassium benzoate), pH adjusters (e.g., sodium hydroxide, hydrochloric acid, tromethamine and organic acids and bases such as citric acid), buffers (e.g. acetic acid and salts, citric acid and salts, boric acid and salts, and phosphoric acid and salts such as mono- and di-potassium phosphate, citric acid/sodium citrate, and dibasic sodium phosphate/citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., glycerin, propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof), skin conditioning agents (e.g., aloe extracts, allantoin, bisabolol, ceramides, dimethicone, hyaluronic acid, and dipotassium glycyrrhizate), sunscreen and/or sunblock compounds, dermatologically acceptable carriers, surfactants, anti-caking agents, anti foaming agents, binders, bulking agents, film formers, opacifying agents, thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes) and combinations of the foregoing. Additional specific examples of the carriers, auxiliaries and/or excipients of the foregoing classes can be found in U.S. Pat. Nos. 9,408,881; 10,286, 030; and 10,493,011 and U.S. Patent Application Publication Nos. 2011/0158922; 2012/0076842; and 2015/0202139 that are incorporated herein by reference. The skilled artisan is aware that some of the carries, auxiliaries and/or excipients may be included in more than one of the foregoing classifications. Stated another way, some of the carriers, auxiliaries and/or excipients may impart one or more properties to the topical composition.

The following provides specific non-limiting examples of some of the additional ingredients that can be used with certain embodiments of the present invention such as the gels, creams, lotions, ointments and serums.

Thickening/Viscosity Enhancing Agents (Including Thickeners and Gelling Agents)

The topical compositions of the present invention can comprise one or more thickening or viscosity enhancing agents. In some embodiments, one or more thickening or viscosity enhancing agent is present at a level of from about 0.05 wt % to about 15 wt %, preferably from about 0.1 wt % to about 10 wt %, and more preferably from about 0.25 wt % to about 7.5 wt %, based on the total weight of the topical composition. Nonlimiting classes of thickening or viscosity enhancing agents include those selected from the following:

a) Carboxylic Acid Polymers

The topical compositions of the present invention can optionally contain polymers that are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Polymers useful in the present invention are more fully described in U.S. Pat. Nos. 5,087,445; 4,509,949; and 2,798,053, and in CTFA International Cosmetic Ingredient Dictionary, Tenth Edition, 2004.

Examples of commercially available carboxylic acid polymers useful herein include the carbomers, which are homopolymers of acrylic acid crosslinked with allyl ethers of sucrose or pentaerytritol. The carbomers are available as the Carbopol® 900 series from Lubrizol (e.g., Carbopol® 934; 940, 941, 971, 974, 980 and 981). In addition, other suitable carboxylic acid polymeric agents include Ultrez® 10 and copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10}$-$C_{30}$ alkyl acrylate crosspolymers and are commercially available as Carbopol® 1342, Carbopol® 1382, Pemulen TR-1, and Pemulen TR-2, from Lubrizol. In other words, examples of carboxylic acid polymer thickeners useful herein are those selected from carbomers, acrylates/$C_{10}$-$C_{30}$ alkyl acrylate crosspolymers, and mixtures thereof.

b) Crosslinked Polyacrylate Polymers

The topical compositions of the present invention can optionally contain crosslinked polyacrylate polymers useful as thickeners or gelling agents including both cationic and nonionic polymers, with the cationics being generally preferred. Examples of useful crosslinked nonionic polyacrylate polymers and crosslinked cationic polyacrylate polymers are those described in U.S. Pat. Nos. 5,100,660; 4,849,484; 4,835,206; 4,628,078; and 4,599,379.

c) Polyacrylamide Polymers

The topical compositions of the present invention can optionally contain polyacrylamide polymers, especially nonionic polyacrylamide polymers including substituted branched or unbranched polymers. Preferred among these polyacrylamide polymers is the nonionic polymer given the CTFA designation polyacrylamide and isoparaffin and laureth-7, available under the Tradename Sepigel 305 from Seppic Corporation.

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc.

d) Polysaccharides

The topical compositions of the present invention can optionally contain a wide variety of polysaccharides. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Other useful polysaccharides include scleroglucans comprising a linear chain of (1-3) linked glucose units with a (1-6) linked glucose every three units, a commercially available example of which is Clearogel™ CS11 from Michel Mercier Products Inc.

e) Gums

The topical compositions of the present invention can optionally contain other thickening and gelling agents which are primarily derived from natural sources. Nonlimiting examples of these thickening and gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

In certain embodiments, the topical compositions of the present invention may include a polymer or co-polymer comprising acryloyldimethyl taurate monomers, such as those described in the Jan. 14, 2016 Safety Assessment of Acryloyldimethyltaurate Polymers Used in Cosmetics, incorporated herein by reference. The polymer or co-polymer comprising acryloyldimethyl taurate monomers may be present in an amount of about 0.05 wt % to about 10 wt %, preferably from about 0.1 wt % to about 7.5 wt %, and more preferably from about 0.5 wt % to about 5.0 wt %, based on the total weight of the topical composition.

Film Forming Agents

The topical compositions of the present invention can comprise one or more film forming agents. In some embodiments, film forming agent and the thickening/viscosity enhancing agent may be the same compound. The film forming agent may be present in an amount of from about 0.05 wt % to about 50 wt %, preferably from about 0.1 wt % to about 40 wt %, and more preferably from about 0.25 wt % to about 30 wt % based on the total weight of the topical composition.

In certain embodiments, the film forming agent may be a silicone containing compound. Silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials.

The silicone containing compounds that can be used in the compositions of the present invention include silicone oils (e.g., volatile and non-volatile oils), gels, and solids. In some embodiments, the silicon containing compounds includes a silicone oil such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application. A "volatile silicone oil" includes a silicone oil having a low heat of vaporization, i.e., normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cps or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

In certain embodiments, the topical composition should comprise one or more emollients. The one or more emollients may be present in an amount of from about 0.05 wt % to about 40 wt %, preferably from about 0.1 wt % to about 35 wt %, and more preferably from about 0.25 wt % to about 30 wt % based on the total weight of the topical composition. Examples of emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids.

Suitable silicone oils for use as emollients include dimethyl polysiloxanes, methyl(phenyl) polysiloxanes, and water-soluble and alcohol-soluble silicone glycol copolymers.

Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate.

Specific examples of alkyl esters of diacids include diisopropyl adipate, diisohexyl adipate, bis(hexyldecyl) adipate, and diisopropyl sebacate.

Other suitable classes of emollients or emulsifiers which may be used in the topical formulations include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Other useful waxes may include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

In certain embodiments, the one or more emollients may comprise a $C_8$-$C_{24}$ alkane or mixtures thereof. The one or more $C_8$-$C_{24}$ alkane emollient may be present in an amount of from about 0.1 wt % to about 10 wt %, preferably from about 0.5 wt % to about 7.5 wt %, and more preferably from about 0.75 wt % to about 5.0 wt % based on the total weight of the topical composition. Examples of suitable $C_8$-$C_{24}$ alkane emollients include but are not limited to: a mixture of $C_9$-$C_{12}$ alkanes, commercially available under the tradename JEECHEM NDA-LC; a mixture of $C_{13}$-$C_{14}$ alkanes, commercially available under the tradename JEECHEM NDA-CC; a mixture of $C_{18}$-$C_{21}$ alkanes, commercially available under the tradename JEECHEM NDA-HC; a mixture of $C_{15}$-$C_{19}$ alkanes, commercially available under the tradename JEECHEM NDA-5C; a $C_{12}$ alkane, commercially available under the tradename JEECHEM NDA-D; a $C_{14}$ alkane, commercially available under the tradename JEECHEM NDA-T; a $C_{18}$ alkane, commercially available under the tradename JEECHEM NDA-O; and a $C_{16}$ alkane, commercially available under the tradename JEECHEM NDA-H. A preferred $C_8$-$C_{24}$ alkane emollient is a solid at room temperature such as a mixture of $C_{18}$-$C_{21}$ alkanes, commercially available under the tradename JEECHEM NDA-HC. JEECHEM NDA-HC comprises less than 0.5% hexadecane; greater than 97% octadecane, less than 1.5% eicosane and less than 1.5% heinicosane; The topical compositions of the present invention may also comprise one or more solvents.

The solvents can include water and/or organic based solvents such as $C_1$-$C_{10}$ mono-alcohols (e.g., methanol, ethanol, isopropanol, benzyl alcohol, phenoxyethanol etc.) $C_2$-$C_{12}$ polyalcohols (e.g., ethylene glycol, propylene glycol, hexylene glycol, glycerin, etc.) or combinations thereof. In certain embodiments, the topical compositions of the present invention comprise about 20 wt % to about 80 wt %, preferably about 30 wt % to about 75 wt % and more preferably about 40 wt % to about 65 wt % based on the total weight of the topical composition of water.

The compositions of the present invention may be prepared by any method commonly known in the industry and may include blending, mixing, emulsifying, heating, cooling steps or any combination thereof. Examples of manufacturing methods can be found in U.S. Pat. No. 10,493,011 and U.S. Patent Application Publication No. 2011/0158922, which are incorporated herein by reference.

The topical compositions of the present invention may be packaged and dispensed in a suitable container. Containers can include a bottle, a tube (metal, plastic or laminate), a pressurized container, or pouches. The containers may include amounts of the topical composition for single or multiple applications. The containers may include indicia on its surface that instruct the subject on its application and use. The instructions for use may also be printed separately and packaged with the container comprising the topical composition.

The containers comprising multiple applications of the topical composition can dispense a pre-determined amount of the topical composition via a metered or calibrated spray, pump, or squeeze mechanism. In other embodiments, the container can be squeezed (e.g., metal, laminate, or plastic tube) to dispense a desired amount of the composition.

In certain embodiments, the subject will apply the desired amount of the topical composition to a clean and preferably dry skin surface such as submental region, abdomen, face, neck, flank, back, chest, arm (such as the upper arm region), leg (such as the thigh region), buttocks or combination thereof at least once a day, preferably twice or thrice a day. In certain embodiments, the subject will apply about 0.25 to about 2.0 grams, preferably 0.30 grams to about 1.5 grams and more preferably about 0.3 grams to about 1.6 grams. The amount will be adjusted depending upon surface area to be treated. In some embodiments, the topical composition in accordance with the present invention may be applied to the target area once, twice or thrice daily for at least 1 day, 2 days, 3 days, 4 days, 5 days, 6 days, 1 week, 2 weeks, 3 weeks, 1 month, 2 months, 3 months, 4 months, 5 months, 6 months, or more. The application of the topical composition to the target area during the treatment course will produce at least a 5%, 6%, 7%, 8%, 9%, 10%, 11%, 12% 13%, 14%, 15%, 16%, 17% 18%, 19%, 20% or more improvement compared to the initial or baseline investigator measurement or assessment of one or more of the following parameters: crepiness, smoothness, tone, texture, firmness, cellulite, sagging or a combination thereof. The application of the topical composition to the target area during the treatment course will produce at least a 5%, 6%, 7%, 8%, 9%, 10%, 11%, 12% 13%, 14%, 15%, 16%, 17% 18%, 19%, 20%, 21%, 22%, 23%, 24%, 25%, 26%, 27%, 28%, 29%, 30%, 31%, 32%, 33%, 34%, 35% or more improvement compared to the initial or baseline instrumental analysis of one or more of the following parameters: skin firmness (extensibility), epidermal and dermal tissue density, skin hydration, attenuation coefficient (tissue density) or a combination thereof.

The topical compositions described herein are useful in conjunction with body shaping procedures, such as non-invasive radiofrequency (RF)-based technology (hot) or cryo-based technologies (cold). RF technology involves electric energy rather than photo-energy, often utilizing skin sparing techniques or insulated needles where these are utilized and thus the epidermis is largely unaffected and untargeted in these situations. Accordingly, the topical compositions in accordance with the present invention are complementary adjuncts to the aforementioned body shaping procedures to enhance the overall outcome of the body shaping procedure. As used herein the term body shaping procedure is intended to include procedures that reduce fat, reduce cellulite and/or reduce skin laxity in a target area.

In some embodiments, the topical compositions in accordance with the present invention are applied to a human subject's outer skin surface prior to a body shaping procedure, during a body shaping procedure, or following a body shaping procedure.

The topical compositions in accordance with the present invention may be applied to a target area of a body shaping procedure as a pre-conditioning treatment of the target area prior to the body shaping procedure. In some embodiments, the topical composition in accordance with the present invention may be applied to the target area once, twice or thrice daily for at least 1 day, 2 days, 3 days, 4 days, 5 days, 6 days, 1 week, 2 weeks, 3 weeks, 1 month, 2 months, 3 months, 4 months, 5 months, 6 months, or more as a pre-conditioning treatment. In some instances, the topical compositions in accordance with the present invention are applied to the target area for at least 1-12 weeks, 1-8 weeks, 1-6 weeks, 1-4 weeks, 1-3 weeks or 1-2 weeks as a pre-conditioning treatment. In some instances, the topical compositions in accordance with the present invention are applied to the target area up to 1 hour, up to 2 hours, up to 3 hours, up to 5 hours, up to 6 hours, up to 7 hours, up to 8 hours, up to 12 hours, up to 16 hours, up to 20 hours, or up to 24 hours prior to the body shaping procedure to enhance dilation of the blood and lymph vessels in the target area and thereby enhance and accelerate the removal of fatty acids and liquids generated during the body shaping procedure.

In some embodiments, the topical compositions in accordance with the present invention may be applied to a target area of a body shaping procedure as a post conditioning treatment of the target area. In some embodiments, the topical composition in accordance with the present invention may be applied to the target area once, twice or thrice daily for at least 1 day, 2 days, 3 days, 4 days, 5 days, 6 days, 1 week, 2 weeks, 3 weeks, 1 month, 2 months, 3 months, 4 months, 5 months, 6 months, following the body shaping procedure as a post conditioning treatment. In some instances, the topical compositions in accordance with the present invention are applied to the target area of the body shaping procedure for at least 1-12 weeks, 1-8 weeks, 1-6 weeks, 1-4 weeks, 1-3 weeks or 1-2 weeks as a post conditioning treatment. In some instances, the topical compositions in accordance with the present invention are applied to the target area up to 1 hour, up to 2 hours, up to 3 hours, up to 5 hours, up to 6 hours, up to 7 hours, up to 8 hours, up to 12 hours, up to 16 hours, up to 20 hours, or up to 24 hours following the body shaping procedure to enhance dilation of the blood and lymph vessels in the target area and thereby enhance and accelerate the removal of fatty acids and liquids generated during the body shaping procedure. In some embodiments, the topical compositions in accordance with the present invention may be applied multiple times, i.e., 2, 3, 4, 5, 6, 7, 8, 9, 10 or more times in the 24-48 hour period following the body shaping procedure to enhance dilation of the blood and lymph vessels in the target area and thereby enhance and accelerate the removal of fatty acids and liquids generated during the body shaping procedure.

The topical compositions in accordance with the present invention when administered prior to, during, or following a body shaping procedure may improve fat reduction, cellulite reduction or skin laxity in the target area. In some instances, reduction is by 5%, 10%, 15%, 20%, 25%, 30%, 35%, 40%, 45%, 50%, 55%, 60%, 65%, 70%, 75%, 80%, 85%, 90%, 95%, or more than 95% as compared to a control or compared to the target area prior to treatment.

The following examples are provided by way of illustration only and are by no means intended to be limiting.

Example 1

Topical compositions in accordance with the present invention may be prepared having the following ingredients:

| INGREDIENT | WEIGHT PERCENT | | |
|---|---|---|---|
| | Preferred | More Preferred | Most Preferred |
| Tripeptide | 0.0001-2.00 | 0.0002-1.00 | 0.0003-0.50 |
| Tetrapeptide | 0.0001-2.00 | 0.0002-1.00 | 0.0003-0.50 |
| ECM Agent | 0.002-5.00 | 0.005-1.50 | 0.007-1.00 |
| CR Agent | 0.0005-2.50 | 0.001-1.50 | 0.0025-1.00 |
| AT Agent | 0.001-10.00 | 0.01-7.50 | 0.050-5.00 |
| Antioxidant | 0.0005-5.00 | 0.0007-4.00 | 0.001-3.00 |
| Thickening Agent | 0.050-15.0 | 0.10-10.0 | 0.25-7.5 |
| Film Forming Agent | 0.050-50.0 | 0.100-40.0 | 0.25-30.0 |
| Water | 30.0-75.0 | 35.0-70.0 | 40.0-65.0 |

The topical compositions summarized in the above table may be a solution, suspension, dispersion, emulsion, gel, cream, lotion, ointment or serum and further comprise conventional topical/cosmetic carriers and excipients such as one or more emollients, chelating agents, humectants, preservatives, pH adjusting agents, buffering agents, organic solvents, surfactants, emulsifiers, sunscreen agents and combinations of the foregoing

Example 2

Topical compositions in accordance with the present invention and particularly topical creams are prepared having the following composition:

| Ingredient | Weight Percent | | | Function |
|---|---|---|---|---|
| | Preferred | More Preferred | Most Preferred | |
| Water | 35-65 | 40-60 | 45-55 | solvent |
| $C_{18}$-$C_{21}$ Alkane | 0-10 | 0.1-7.5 | 1-5 | skin conditioning agent |
| *Coffea Arabica* (Coffee) Seed Oil | 0.01-10 | 0.25-7.5 | 0.5-5 | skin conditioning agent |
| Sodium Acrylate/Sodium Acrylolydimethyl Taurate Copolymer | 0.1-10 | 0.25-7.5 | 0.5-5 | film former viscosity increasing agent |
| *Brassica Campestris* (Rapeseed) Sterols | 0.01-7.5 | 0.25-5 | 0.5-2.5 | skin conditioning agent |
| *Zingiber Officinale* (Ginger) Root Extract | 0-3 | 0.01-2 | 0.05-1.5 | skin conditioning agent |
| *Oenanthe Javanica* Extract | 0-2 | 0.005-1.5 | 0.01-1 | skin protectant |
| *Chlorella Vulgaris* Extract | 0.001-1 | 0.005-0.75 | 0.0075-0.5 | skin conditioning agent |
| *Melissa Officinalis* Leaf Extract | 0.001-1 | 0.005-0.75 | 0.0075-0.5 | skin conditioning agent |
| *Lentinus Edodes* Extract | 0.001-1 | 0.005-0.75 | 0.0075-0.5 | skin conditioning agent |
| Hydrolyzed Rice Protein | 0.0001-0.07 | 0.0005-0.05 | 0.0007-0.02 | skin conditioning agent |
| *Chlorella Vulgaris*/*Lupinus Albus* Protein Ferment | 0.0001-0.07 | 0.0005-0.05 | 0.0007-0.02 | skin conditioning agent |
| *Coleus Forskohlii* Root Extract | 0.0001-0.07 | 0.0005-0.05 | 0.0007-0.02 | skin conditioning agent |
| Acetyl Tetrapeptide-2 | 0.0001-0.5 | 0.0002-0.1 | 0.0003-0.05 | skin conditioning agent |
| Trifluoracetyl Tripeptide-2 | 0.00001-0.05 | 0.00005-0.01 | 0.00007-0.005 | skin conditioning agent |

The topical compositions described in the above table may further comprise one or more conventional topical/cosmetic carriers and excipients such as one or more emollients, chelating agents, humectants, preservatives, pH adjusting agents, buffering agents, organic solvents, surfactants, emulsifiers, sunscreen agents and combinations of the foregoing. Examples of the one or more conventional topical/cosmetic carriers and excipients that may be included in the topical compositions described in the above table include but are not limited to: one or more skin conditioning agents such as dimethicone, glycerin, butylene glycol, bis-PEG-12 dimethicone, isohexadecane, ethylhexylglycerin, caffeine, caprylyl glycol and combinations thereof; one or more film forming agents such as silicone compounds and polyorganosiloxanes as previously described; one or more solvents such as butylene glycol, propanediol, ethanol, isohexadecane, hexylene glycol, and combinations thereof; one or more preservatives such as phenoxyethanol, caprylyl glycol, potassium benzoate, potassium sorbate, sodium benzoate, sodium sorbate, and combinations thereof; one or more surfactants, solubilizing agents or emulsifying agents such as decyl glucoside, polysorbate (i.e., polysorbate 80), sorbitan oleate, and combinations thereof; one or more chelating agents such as disodium EDTA, phytic acid, citric acid and combinations thereof; one or more antioxidants such as tocopherols, hydroxyacetaphenone, BHA, BHT, propyl gallate and combinations thereof; one or more pH adjusting agents and/or buffering agents such as tromethamine, sodium citrate, citric acid and combinations thereof; one or more binders such as dextran; one or more dispersing agents such as silica; one or more anticaking agents such as HDI-trimethylol hexyllactone crosspolymer; one or more opacifying agents such as polymethylsilsesquioxane; one or more fragrances; and combinations of the foregoing.

Example 3

In vitro and ex vivo studies employing a topical composition as described in Example 2 were conducted to determine the efficacy of the topical compositions of the present invention. The skin rejuvenation efficacy was assessed at a molecular biology level using quantitative real-time PCR (described in detail below).

In Vitro Studies

In vitro studies were conducted using human 3-D skin models that were irradiated with ultra-violet (UV) light to mimic extrinsic skin aging prior to the application of a topical composition as described in Example 2. Specifically, an EpiDermFT™ 3D full thickness human skin model (EFT-400) from MatTek Corp. Tissues were cultured with EpiDermFT Assay Media (EFT-400-MM, MatTek Corp). EpiDermFT was irradiated with 200 mJ/cm$^2$ ultraviolet (UV) light with UV-B filter UV lamp (Honle, Germany) to indicate an extrinsic aging model, followed by topical application of 15 μL of a topical composition as described in Example 2 or dH$_2$O (control), and incubated at 37° C. and 5% CO$_2$ for 24 hours. After incubation five tissues of each condition were placed into RNAlater® solution (ThermoFisher Scientific).

Gene expression results for UV-irradiated, non-treated tissues and UV-irradiated, Example 2-treated tissues relative quantity assessment were compared to non-UV-irradiated, non-treated control tissues after normalized with housekeeping gene GAPDH. Expression levels of genes encoding collagens (COL1A1, COL3A1, COL4A1, COL5A1, COL6A1, and TGFβ1), elastic fiber proteins (ELN and FBN1) were assessed. The results are shown in FIG. 1A wherein a topical composition as described in Example 2 is designated "F19". Application of a topical composition as described in Example 2 resulted in significant upregulation of all genes tested compared to UV-irradiated, non-treated samples indicating that the topical compositions of the present invention stimulate ECM components for dermal structure improvement that may translate into firmer skin, as well as improvement of the dermal-epidermal junction (DEJ) which is important for skin elasticity.

Figure 1B:
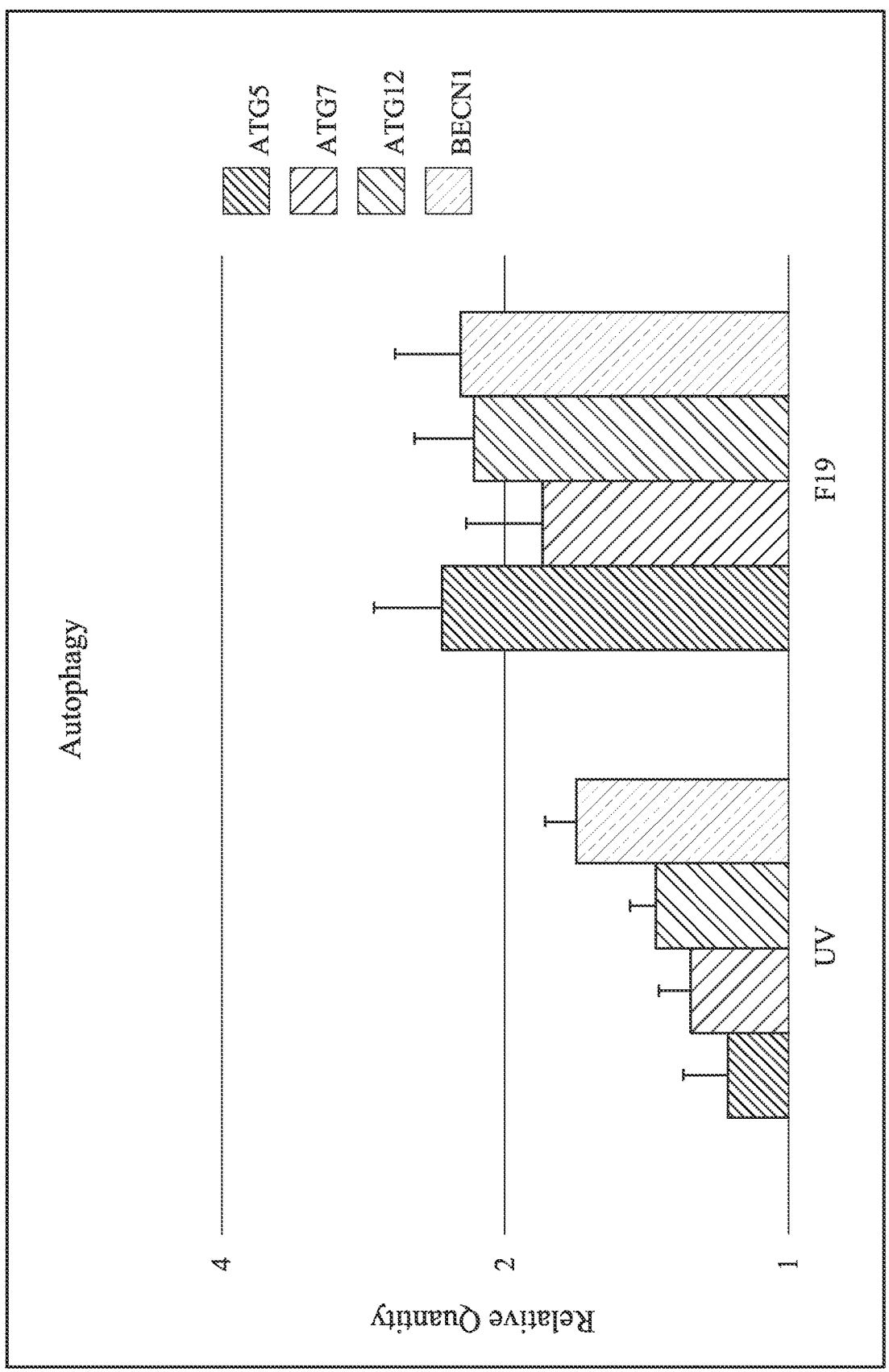
Figure 1C:
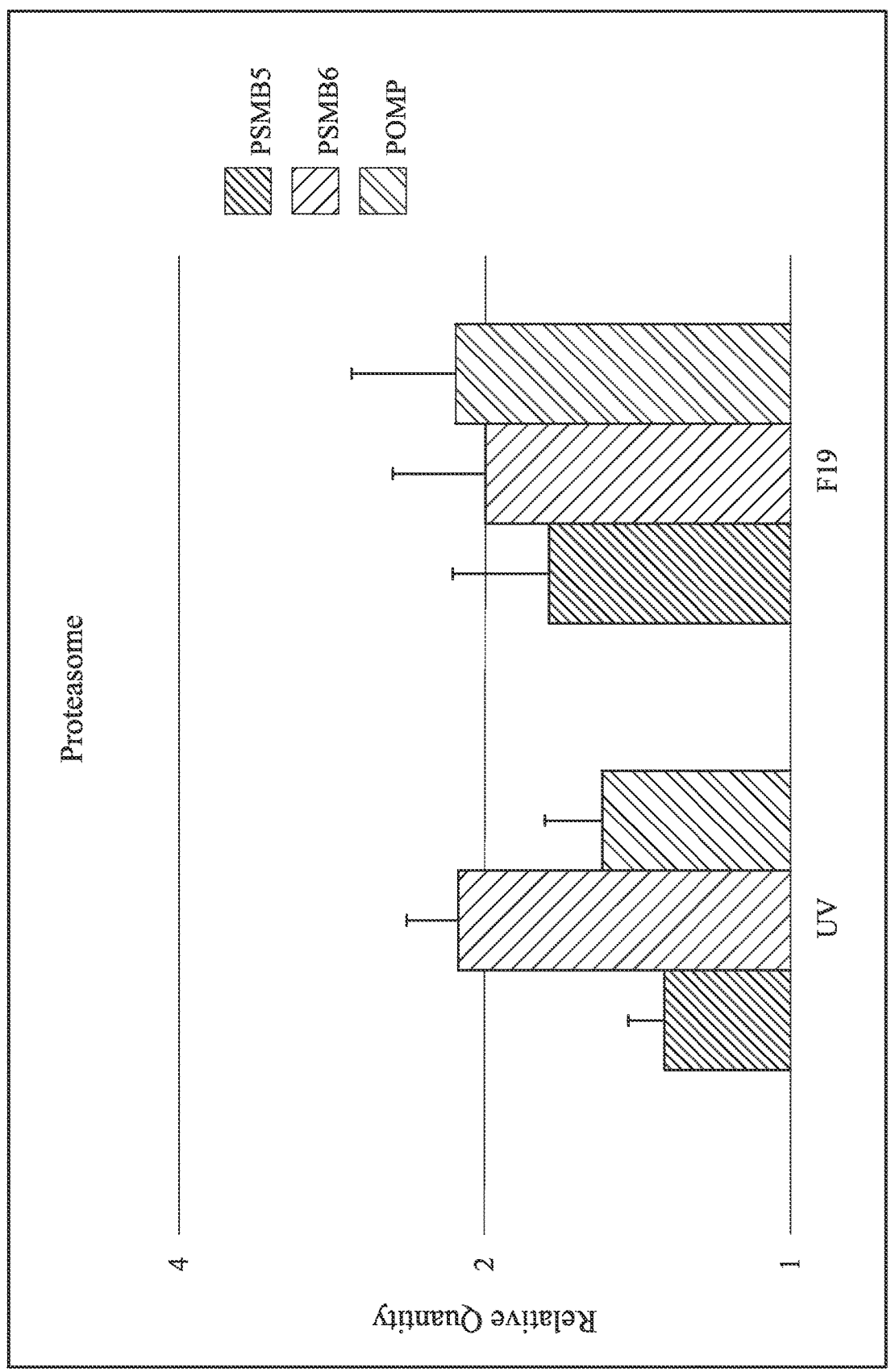

Aging alters essential processes involved in maintaining cellular proteostasis (protein homeostasis), including the proteasome and the autophagy systems, leading to an accumulation in cellular debris, protein aggregation, and cellular damage. As shown in FIGS. 1B and 1C, gene expression levels of key recycling genes involved in proteasome activity (POMP, PSMB5 and PSMB6) and autophagy (ATG5, ATG7, ATG12 and BECN1) were increased with a topical composition as described in Example 2 (designated as "F19"), indicating stimulation of the various cellular recycling processes.

Figure 1D:
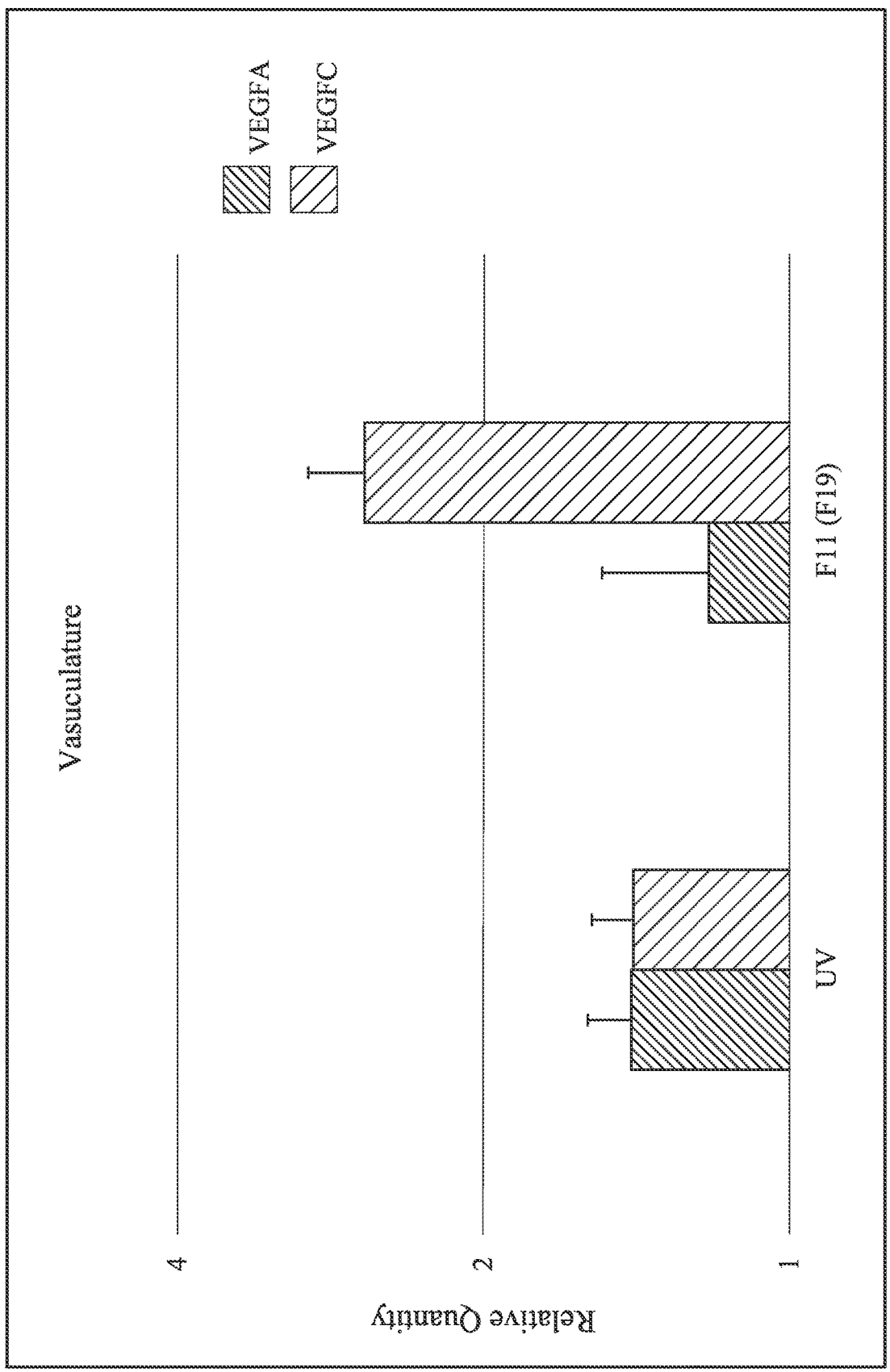

Vasculature genes such as VEGFA for blood vessels and VEGFC for lymphatic vessels were assessed. These genes take a role in vessels quality improvement, especially upregulation of VEGFC which is thought to be involved with activating lymphatic drainage by improving lymphatic vessel quality. FIG. 1D reports the gene expression levels for VEGFA and VEGFC and shows upregulation of these genes with a topical composition as described in Example 2 (designated as "F19").

Figure 1E:
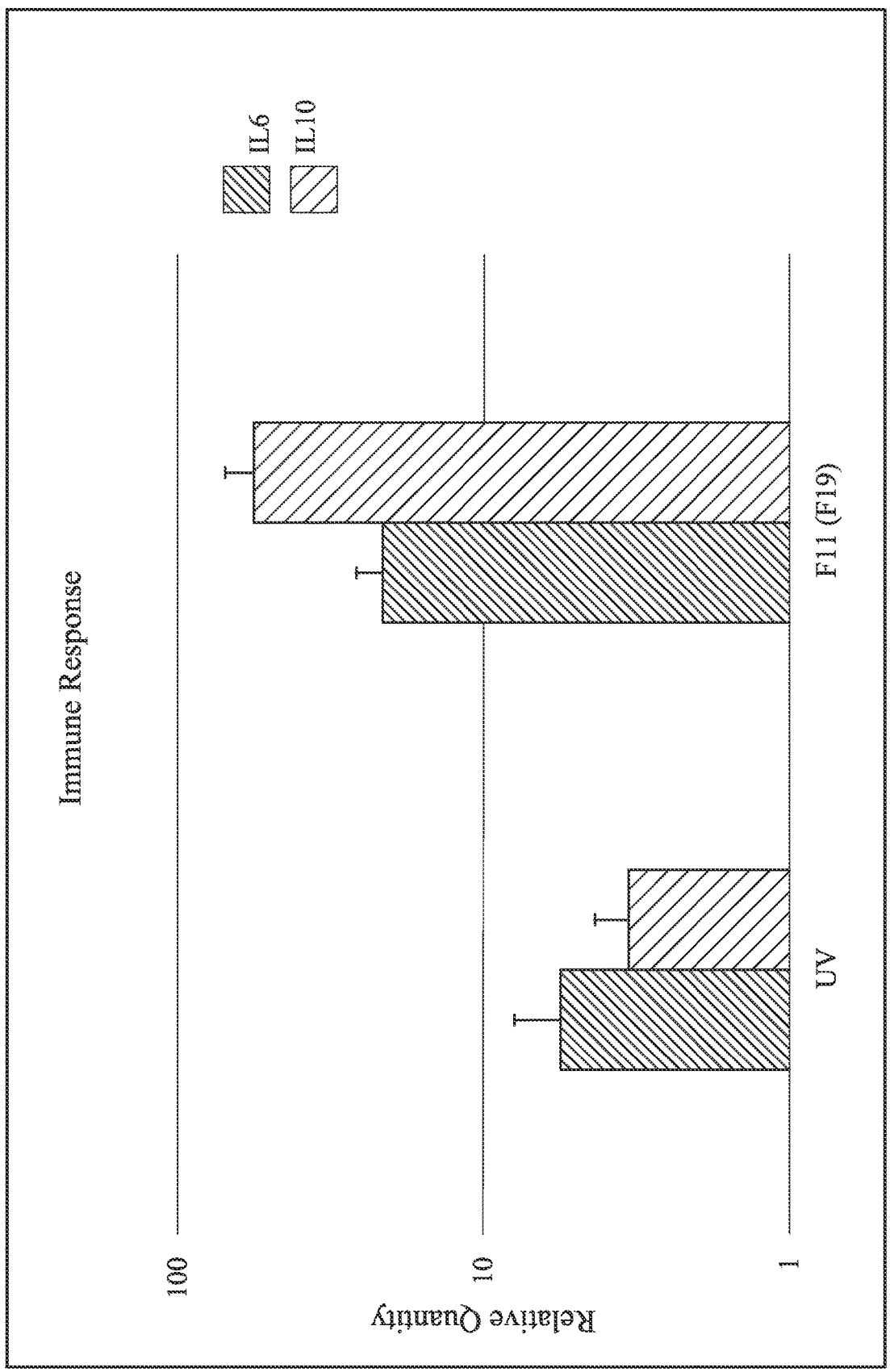

Inflammation biomarkers were also investigated. As shown in FIG. 1E, inflammation gene IL6 and anti-inflammation gene IL10 were investigated and the upregulation of IL10 as shown in FIG. 1E indicates the inflammation response is controlled by application of a topical composition as described in Example 2 (designated as "F-19").

The in vitro pre-clinical data demonstrates the efficacy of the topical composition of the present invention in providing overall skin rejuvenation benefits by boosting various ECM and DEJ components as well as supporting systems that help maintain proteostasis, vasculature and anti-inflammation.

Ex Vivo Studies

Ex vivo studies were conducted to evaluate lipogenesis, lipolysis and adipose metabolism activities. Ex vivo model Hyposkin (HS-001) from Genoskin Inc. were employed for an assessment with application of a topical composition as described in Example 2 (designated as "F19"). Hyposkin consists of surgically removed human abdominal skin with adipose tissues, cultured with Genoskin proprietary culture medium. After 2 hours equilibrating tissues with the culture medium, 15 uL a topical composition as described in Example 2 and dH2O for control were applied on tissues (Day 0) and incubated at 37° C. and 5% CO$_2$ incubator. The topical composition was reapplied every 24 hours for additional two days (Day 1 and Day 2) and at same time culture medium was exchanged. At Day 3, three tissues of each condition were collected and placed into RNAlater® solution (ThermoFisher Scientific) for gene expression analysis.

Figure 2A:
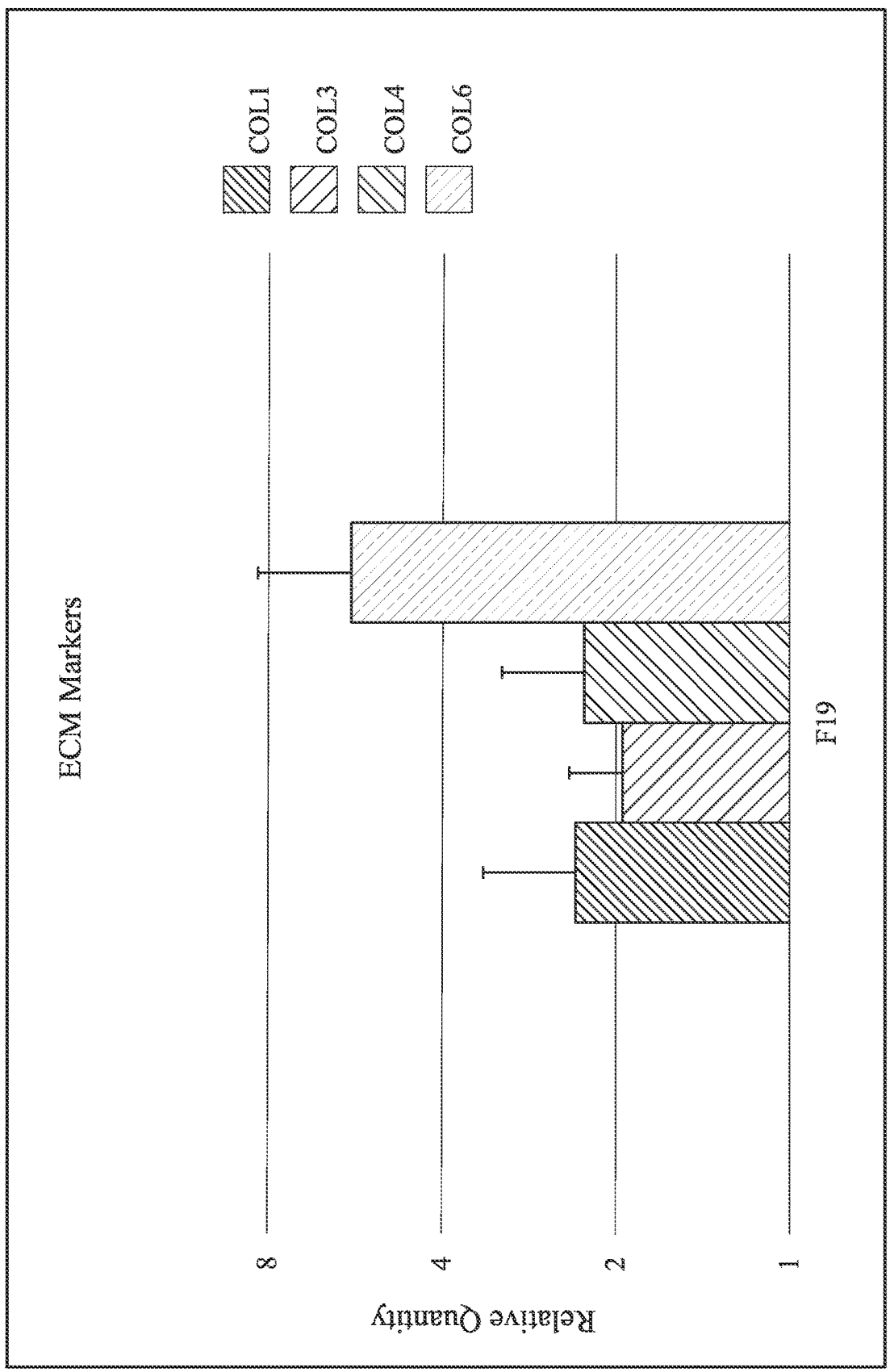
FIGS. 2A-2D show the results of the ex vivo tests described in Example 3.

Gene expression results for three days of Example 2-treated tissues were compared to dH2O treated control tissues after normalization with housekeeping gene GAPDH. Expression levels of genes encoding collagens (COL1A1, COL3A1, COL4A1 and COL6A1) were assessed. The results are shown in FIG. 2A. Application of a topical composition as described in Example 2 resulted in significant upregulation of all genes tested compared to the control.

Figure 2B:
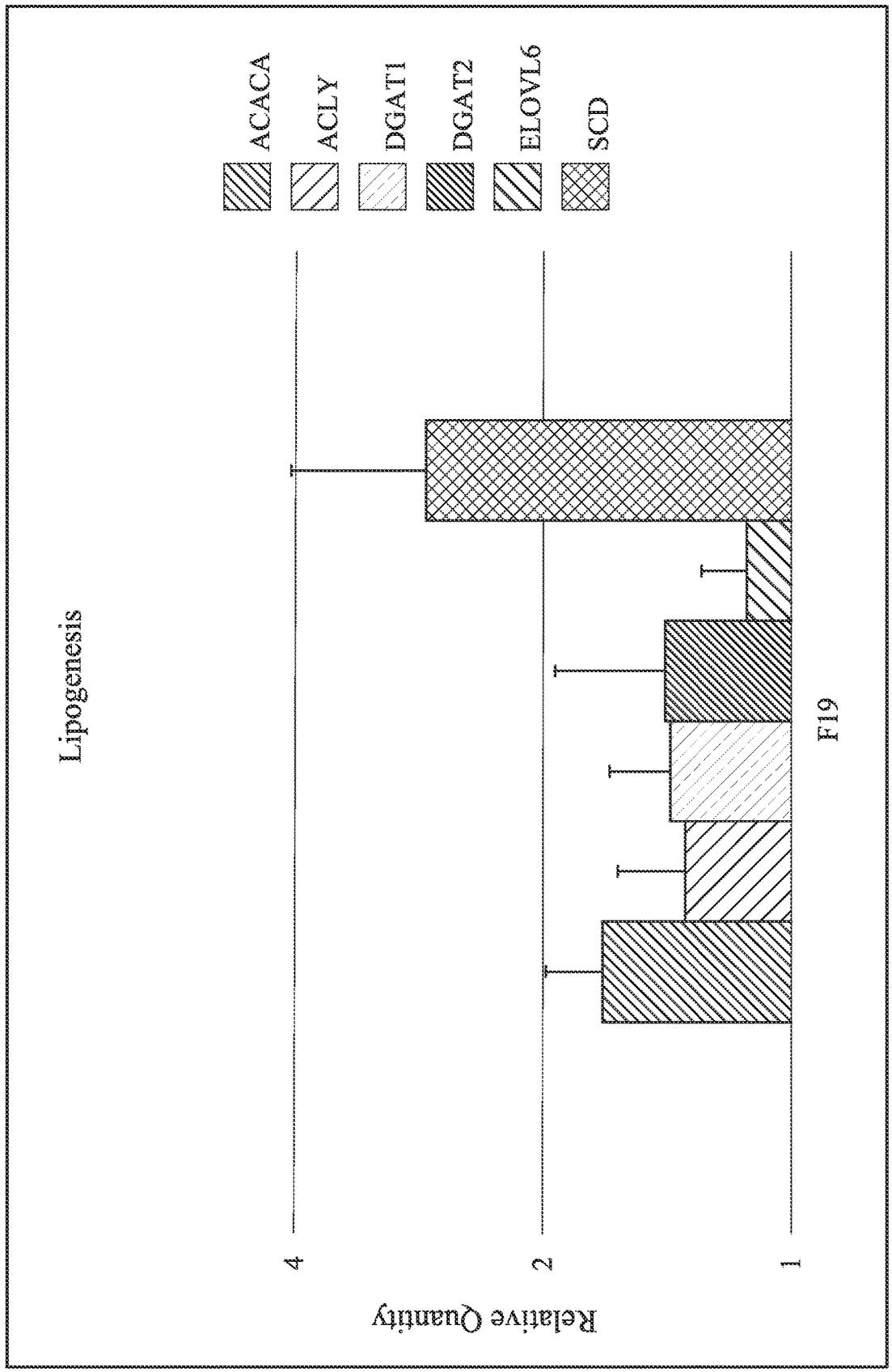
Figure 2C:
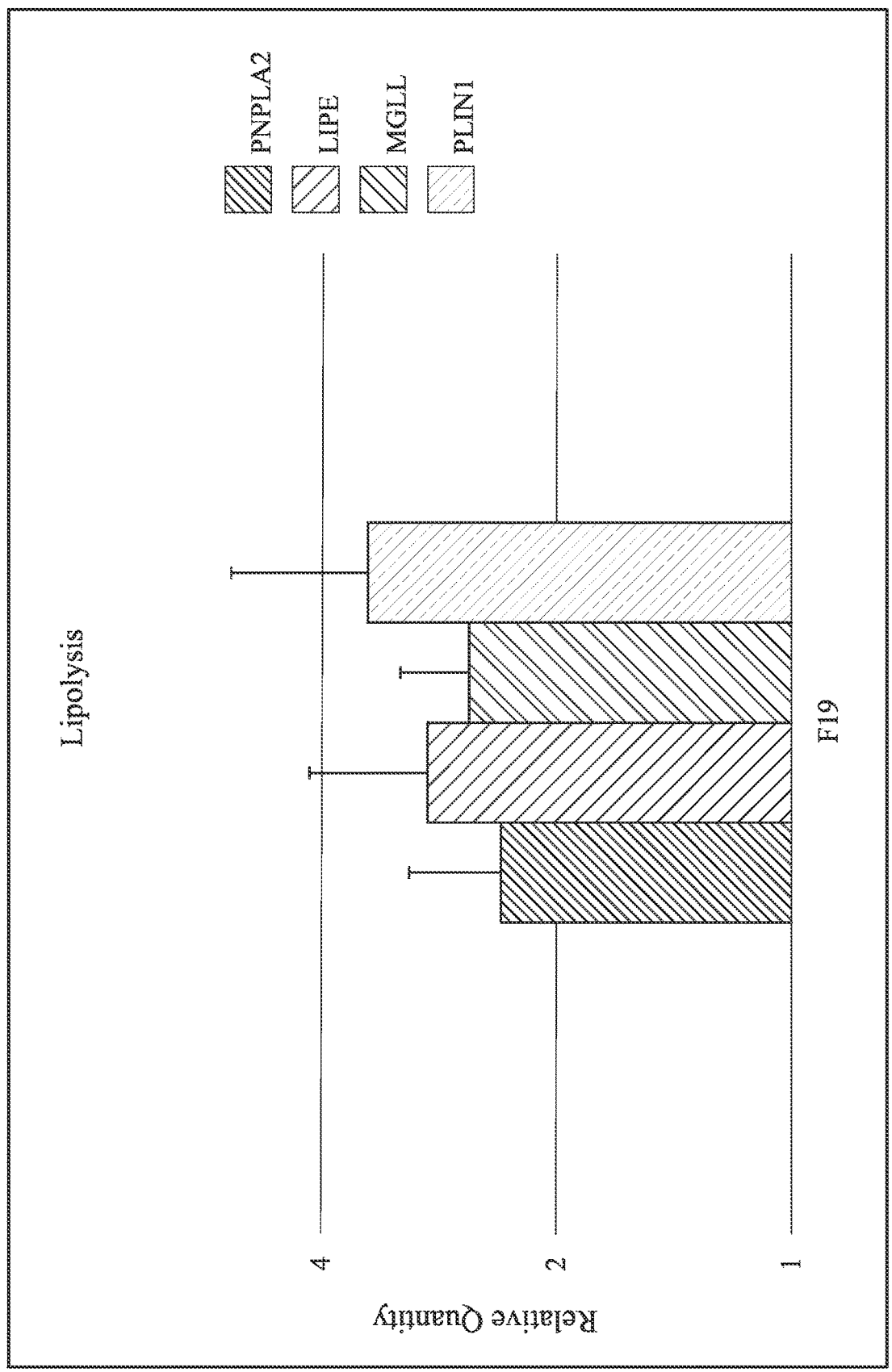
Figure 2D:
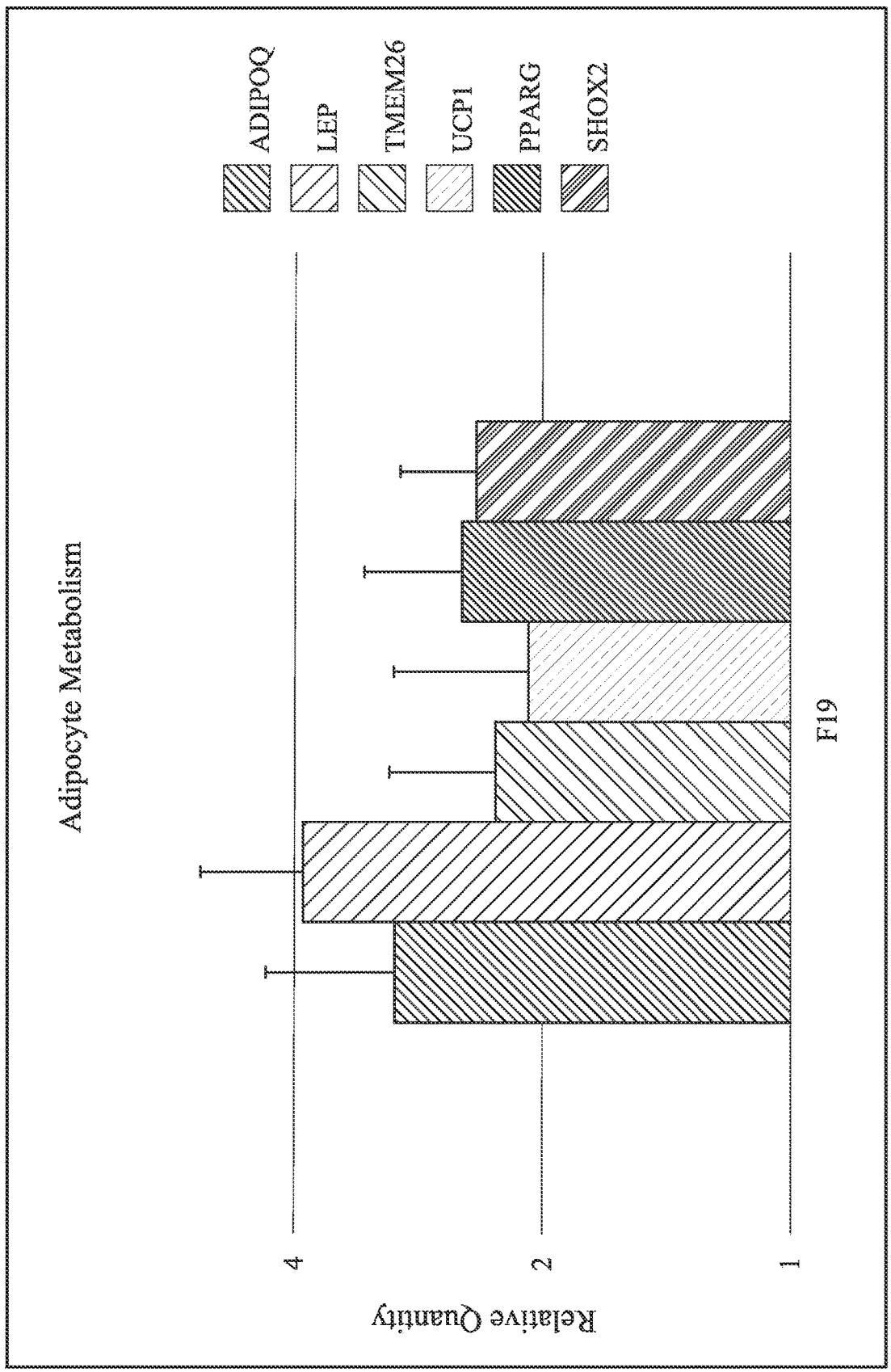

Gene expression result of lipolysis pathway genes, ACACA and ACLY for fatty acid synthesis, DGAT1 and DGAT2 for glycerol lipid synthesis, EVOVL6 and SCD for lipid maturation, indicated an upregulation of all genes as shown in FIG. 2B. However, these upregulations were significantly lower than lipolysis pathway genes PNPLA2, LIP and MGLL which are lipolysis enzymes and membrane protein PLIN1 as shown in FIG. 2C, These results indicate that lipolysis activity is predominant compare to lipogenesis within the tissues, In addition, adipose metabolism related genes ADIPOQ, LEP, TMEM26, UCP1, PPARG and SHOX2 result in significant upregulation.

The ex vivo pre-clinical data demonstrates the efficacy of the topical compositions of the present invention that provides induction of adipose tissues activities by significant upregulation of adipose metabolism related genes.

Quantitative Real-Time PCR mRNA was extracted from the human skin model and human skin ex vivo tissues (Maxwell® RSC simplyRNS Tissue Kit; Promega) followed by cDNA synthesis (High-Capacity cDNA Reverse Transcription Kit; ThermoFisher Scientific) and quantitative real-time PCR (TaqMan Fast Advanced Master Mix, ThermoFisher Scientific). Gene expression analyses were performed using TaqMan Gene Expression Assays (ThermoFisher Scientific) with real-time PCR system QuantStudio7 Flex (ThermoFisher Scientific). The assay mix used for studies are listed in TABLE 1:

group applied the designated composition twice daily (morning and evening) on the front and back of thighs. Included patients were females 30-65 years of age with a Fitzpatrick skin type I-V, mild to moderate cellulite on the backs of the thighs, and body mass index ("BMI") 19-30 $kg/m^2$ with a willingness to maintain a BMI±2 $kg/m^2$ within baseline during the duration of the study. Investigator assessments, instrumentation evaluations, and patient questionnaires were performed. Characteristics and outcomes were summarized descriptively. Changes from baseline were evaluated with a paired t test or Wilcoxon signed-rank test, as appropriate. Comparisons between treatments were evaluated with a 2-sample t test or Wilcoxon rank-sum test, as appropriate.

The topical composition of Example 2 comprised water, disodium EDTA, BPD-500, PLANTAREN 2000 N UP, tromethamine, GRANHYDROSIL PSQ-W-GL, GRANSIL SIW-066, bis-PEG-12-dimethicone, EUXYL PE9010, hydroxyacetaphenone, PROGELINE, CHLORELLAGEN DP, ACTIFOL, RECYCOLL 180, PROLIXIR-ICE, UPLEVITY, *Zingiber officinale* (ginger) root extract, ISONARI, *Coffea arabica* (coffee) seed oil, *Brassica campestris* (rapeseed) sterols, CELLACTIVE SHAPE, $C_{18}$-$C_{21}$ alkanes, citrus paradise (grapefruit) peel oil, and SIMULGEL EG. The vehicle control comprised Water/Aqua/Eau, Sodium Acrylate/Sodium Acryloyldimethyl Taurate Copo-

TABLE 1

| Category | Gene ID | Gene name | Primers Cat# |
|---|---|---|---|
| House keeping | GAPDH | glyceraldehyde-3-phosphate dehydrogenase | Hs02786624_g1 |
| Extracellular | COL1A1 | collagen type 1 alpha 1 | Hs00164004_m1 |
| Matrix | COL3A1 | collagen type 3 alpha 1 | Hs00943809_m1 |
|  | COL4A1 | collagen type 4 alpha 1 chain | Hs00164310_m1 |
|  | COL5A1 | collagen type 5 alpha 1 | Hs00609133_m1 |
|  | COL6A1 | collagen type 6 alpha 1 | Hs01095585_m1 |
|  | ELN | elastin | Hs00355783_m1 |
|  | FBN1 | fibrillin 1 | Hs00171191_m1 |
|  | TGFB1 | transforming growth factor beta 1 | Hs00998133_m1 |
| Vasculature | VEGFA | vascular endothelial growth factor | Hs00900055_m1 |
|  | VEGFC | vascular endothelial growth factor | Hs01099203_m1 |
| Immune | IL6 | interleukin 6 | Hs00174131_m1 |
| Response | IL10 | interleukin 10 | Hs01064648_m1 |
| Autophagy | ATG5 | Autophagy related 5 | Hs00169468_m1 |
|  | ATG7 | Autophagy related 7 | Hs00893766_m1 |
|  | ATG12 | Autophagy related 12 | Hs04980076_s1 |
|  | BECN1 | Beclin 1 | Hs01007018_m1 |
| Proteosome | PSMB5 | proteasome subunit beta 5 | Hs00605652_m1 |
|  | PSMB6 | proteasome subunit beta 6 | Hs00382586_m1 |
|  | POMP | proteasome maturation protein | Hs01106088_m1 |
| Lipogenesis | ACACA | Acetyl-CoA carboxylase | Hs01046047_m1 |
|  | ACLY | ATP citrate lyase | Hs00982738_m1 |
|  | DGAT 1 | Diacylglycerol O-acyltransferase 1 | Hs01020362_g1 |
|  | DGAT 2 | Diacylglycerol O-acyltransferase 2 | Hs01045913_m1 |
|  | ELOVL 6 | Elongation of very long chain fatty acids protein 6 | Hs00907564_m1 |
|  | SCD | Stearoyl-CoA desaturase | Hs01682761_m1 |
| Lipolysis | PNPLA2 | Adipose triglyceride lipase (ATGL) | Hs00982042_m1 |
|  | LIPE | Lipase E, Hormone sensing lipase (HSL) | Hs00943410_m1 |
|  | MGLL | Monoacylglycerol lipase | Hs00996004_m1 |
|  | PLIN1 | Perilipin 1 | Hs00160173_m1 |
| Adipose | ADIPOQ | adiponectin, C1Q and collagen domain containing | Hs00605917_m1 |
| Metabolism | LEP | leptin | Hs00174877_m1 |
|  | TMEM26 | transmembrane protein 26 | Hs00415619_m1 |
|  | UCP1 | uncoupling protein 1 | Hs01084772_m1 |
|  | PPARG | peroxisome proliferator activated receptor gamma | Hs01115513_m1 |
|  | SHOX2 | short stature homeobox 2 | Hs00243203_m1 |

Example 4

A double-blind, randomized, 12-week study comparing a topical composition as described in Example 2 and a vehicle control was conducted. Patients assigned to either treatment lymer, Disodium EDTA, Ethylhexylglycerin, Hydroxyacetophenone, Isohexadecane, Phenoxyethanol and Polysorbate 80.

Forty-four patients completed treatment (Example 2, 30; vehicle control, 14). Patients randomized to Example 2 group showed significant improvements in the thighs (all P<0.05) at week 12 compared with baseline for investigator assessments of crepiness (20.2%), skin smoothness (19.3%), skin tone evenness (9.2%), body skin texture (14.1%), body skin firmness (12.1%), and cellulite (14.1%). Significant improvements (all P<0.05) were also achieved by the Example 2 composition at week 12 compared with vehicle control for thigh crepiness (20.2% vs 10.7%), body skin texture (14.1% vs 7.0%), and skin tone evenness (9.2% vs 3.0%). Significant improvements in the thighs (all P<0.05) at week 12 compared with baseline in patients randomized to Example 2 group were observed for instrumentation analyses of skin firmness (extensibility, 15.0%) and epidermal and dermal tissue density (29.5%), and for attenuation coefficient, which reflects tissue density (31.6%). The improvements in investigator and instrument assessments of skin efficacy parameters at week 12 were accompanied by significant improvements in self-perceived efficacy (P<0.02) and overall satisfaction with the appearance of their skin following treatment with the composition of Example 2 versus vehicle control.

The investigator assessment consisted of grading of the following parameters: body skin firmness, body skin texture, crepiness, sagging, skin tone evenness, skin smoothness (tactile), cellulite global grading scale (thighs only).

The instrument analysis consisted of corneometer measurements (hydration), cutometer measurements (skin firmness and laxity), ultrasound measurements (skin density), optical coherence tomography (skin structure) and Antera 3D imaging (topography).

The topical composition in accordance with the present invention, and Example 2 in particular, provided significant improvements in the thighs compared with baseline and vehicle control across multiple investigator assessment and instrumentation evaluation parameters while improving self-reported efficacy and satisfaction in the majority of patients.

Example 5

A double-blind, randomized, 12-week study comparing a topical composition as described in Example 2 and a vehicle control was conducted. Patients assigned to either treatment applied the designated composition twice daily (morning and evening) on the upper arms. Included patients were females 30-65 years of age with a Fitzpatrick skin type I-V, mild to moderate visual lack of firmness and sagging on the upper arms, and BMI of 19-30 kg/m$^2$ with a willingness to maintain the BMI±2 kg/m$^2$ within baseline. Investigator assessments, instrumentation evaluations, and patient questionnaires were performed. Characteristics and outcomes were summarized descriptively. Changes from baseline were evaluated with a paired t test or Wilcoxon signed-rank test, as appropriate. Comparisons between treatments were evaluated with a 2-sample t test or Wilcoxon rank-sum test, as appropriate.

The topical composition of Example 2 comprised water, disodium EDTA, BPD-500, PLANTAREN 2000 N UP, tromethamine, GRANHYDROSIL PSQ-W-GL, GRANSIL SIW-066, bis-PEG-12-dimethicone, EUXYL PE9010, hydroxyacetaphenone, PROGELINE, CHLORELLAGEN DP, ACTIFOL, RECYCOLL 180, PROLIXIR-ICE, UPLEVITY, *Zingiber officinale* (ginger) root extract, ISONARI, *Coffea arabica* (coffee) seed oil, *Brassica campestris* (rapeseed) sterols, CELLACTIVE SHAPE, $C_{18}$-$C_{21}$ alkanes, citrus paradise (grapefruit) peel oil, and SIMULGEL EG. The vehicle control was the same as described in Example 4.

Forty-four patients completed treatment (Example 2, 30; vehicle control, 14). Patients randomized to the Example 2 group showed significant improvements in the upper arms (all P<0.05) at week 12 compared with baseline for investigator assessments of crepiness (21.7%), skin smoothness (24.3%), skin tone evenness (8.9%), body skin texture (14.8%), body skin firmness (8.2%), and sagging (5.4%). Significant improvements in the upper arms (all P<0.05) at week 12 compared with baseline in patients randomized to Example 2 group were observed for instrumentation analyses of skin firmness (extensibility, 16.4%) and epidermal and dermal tissue density (19.4%), and for skin hydration (15.5%). The improvements in investigator and instrument assessments of skin efficacy parameters at week 12 were accompanied by significant improvements in self-perceived efficacy (P<0.02) and overall satisfaction with the appearance of their skin following treatment with the topical composition of Example 2 versus vehicle control.

The investigator assessment consisted of grading of the following parameters: body skin firmness, body skin texture, crepiness, sagging, skin tone evenness, skin smoothness (tactile), cellulite global grading scale (thighs only).

The instrument analysis consisted of corneometer measurements (hydration), cutometer measurements (skin firmness and laxity), ultrasound measurements (skin density), optical coherence tomography (skin structure), and Antera 3D imaging (topography).

The topical composition in accordance with the present invention, and Example 2 in particular, provided significant improvements in the upper arms compared with baseline and vehicle control across multiple investigator assessment and instrumentation evaluation parameters while improving self-reported efficacy and satisfaction in the majority of patients.

Example 6

An open-label, single center study was conducted to assess the efficacy and tolerability of a topical composition as described in Example 2 on subjects who had received a body contouring procedure on the inner thighs, posterior axillary (back bra fat) and/or submental areas. The study was conducted for 12 weeks. Subjects received either COOLSCULPTING® (n=8) or COOLSCULPTING® ELITE (n=9) procedures at baseline, and one subject received a second COOLSCULPTING® ELITE procedure at week 6 of the study. After the body contouring procedure and baseline evaluation, subjects were instructed to apply the topical composition as described in Example 2 twice a day (AM and PM) for 12 weeks on the contouring treated area. Seventeen subjects (16 females and 1 male) between the ages of 25-63 participated in the study (41% Caucasian, 29% African American, 24% Hispanic and 6% Asian). The subjects had a Fitzpatrick Skin Type of II-VI (18% type II, 41% type III, 18% type IV, 12% type V and 12% type VI). Five (5) subjects had the contouring procedure and topical composition application on the frontal neck and submental area; six subjects (6) had the contouring procedure and topical composition application on the posterior upper and inner thighs area and six (6) subjects had the contouring procedure and topical composition application on the posterior axillary (back bra fat) area. Investigator assessments were performed and subject self-assessment questionnaires were obtained.

The topical composition of Example 2 comprised water, disodium EDTA, BPD-500, PLANTAREN 2000 N UP, tromethamine, GRANHYDROSIL PSQ-W-GL, GRANSIL SIW-066, bis-PEG-12-dimethicone, EUXYL PE9010, hydroxyacetaphenone, PROGELINE, CHLORELLAGEN DP, ACTIFOL, RECYCOLL 180, PROLIXIR-ICE, UPLEVITY, *Zingiber officinale* (ginger) root extract, ISONARI, *Coffea arabica* (coffee) seed oil, *Brassica campestris* (rapeseed) sterols, CELLACTIVE SHAPE, $C_{18}$-$C_{21}$ alkanes, citrus paradise (grapefruit) peel oil, and SIMULGEL EG.

The investigator assessment results are summarized in the following table wherein a "+" indicates a statistically significant improvement vs. baseline.

| Body Contouring Area | Investigator Assessments | Week 2 | Week 6 | Week 12 |
|---|---|---|---|---|
| Frontal Neck and Submental Areas | Body Skin Firmness |  | + | + |
|  | Body Skin Texture |  | + | + |
| Posterior Upper and Inner Thighs | Body Skin Firmness | + | + | + |
|  | Body Skin Texture | + | + | + |
| Posterior Axillary (Back Bra Fat) | Body Skin Firmness | + | + | + |
|  | Body Skin Texture | + | + | + |
| Paired t-test p-value |  | All p ≤ 0.02 | All p ≤ 0.057 | All p ≤ 0.009 |

Figure 3A:
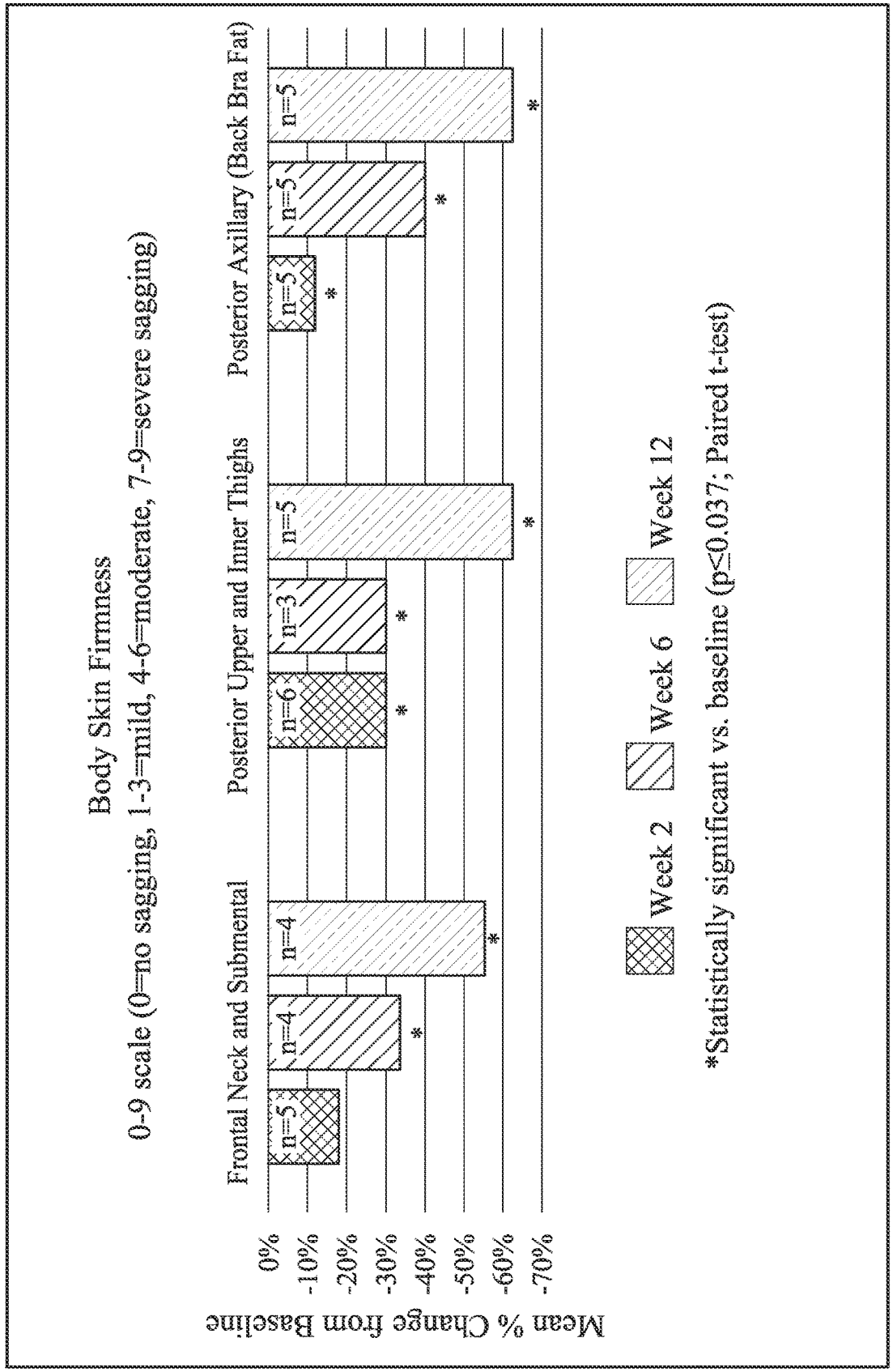
FIGS. 3A-3G show the results of the investigator assessments form the study described in Example 6.
Figure 3B:
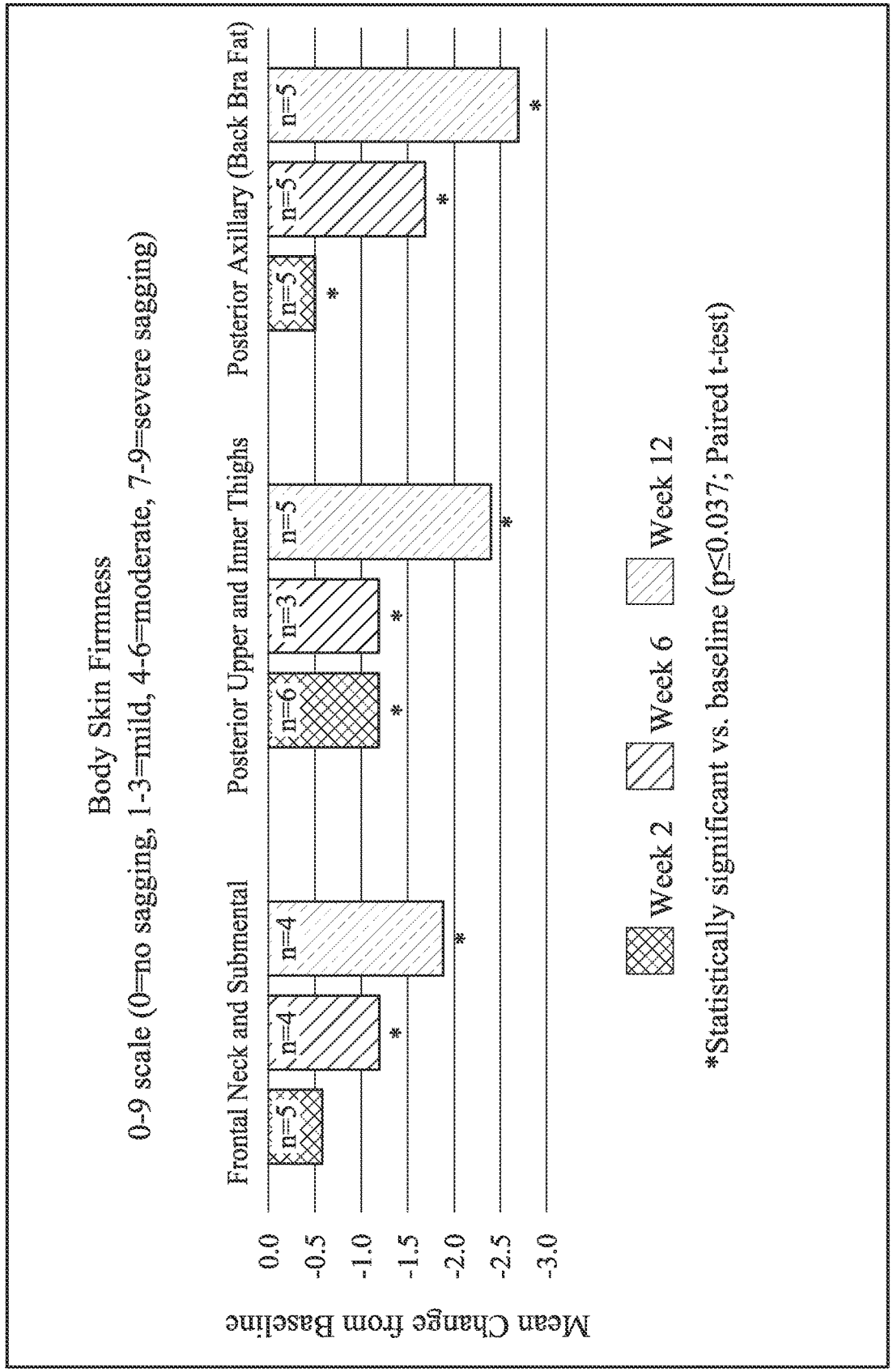
Figure 3C:
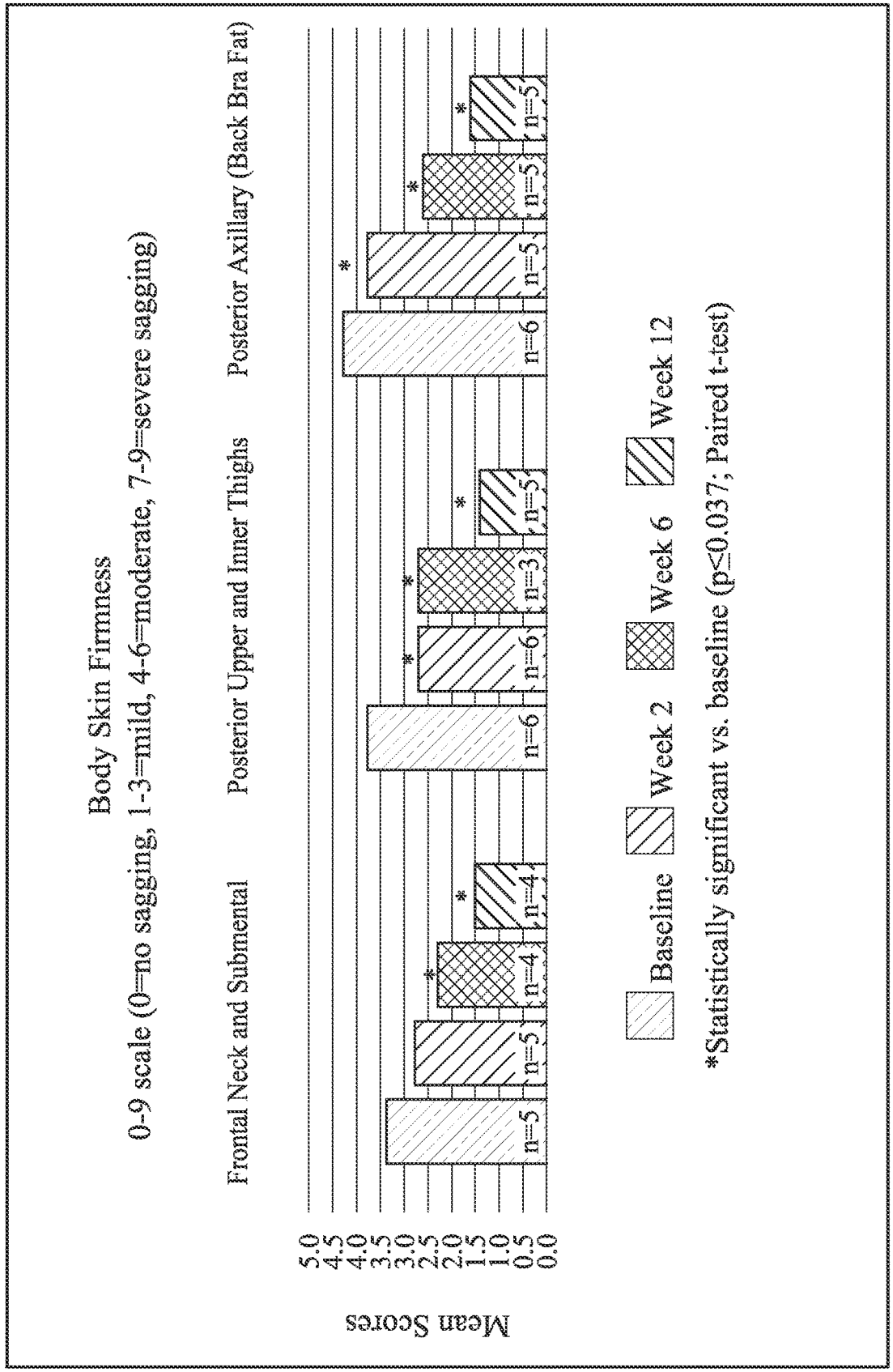
Figure 3D:
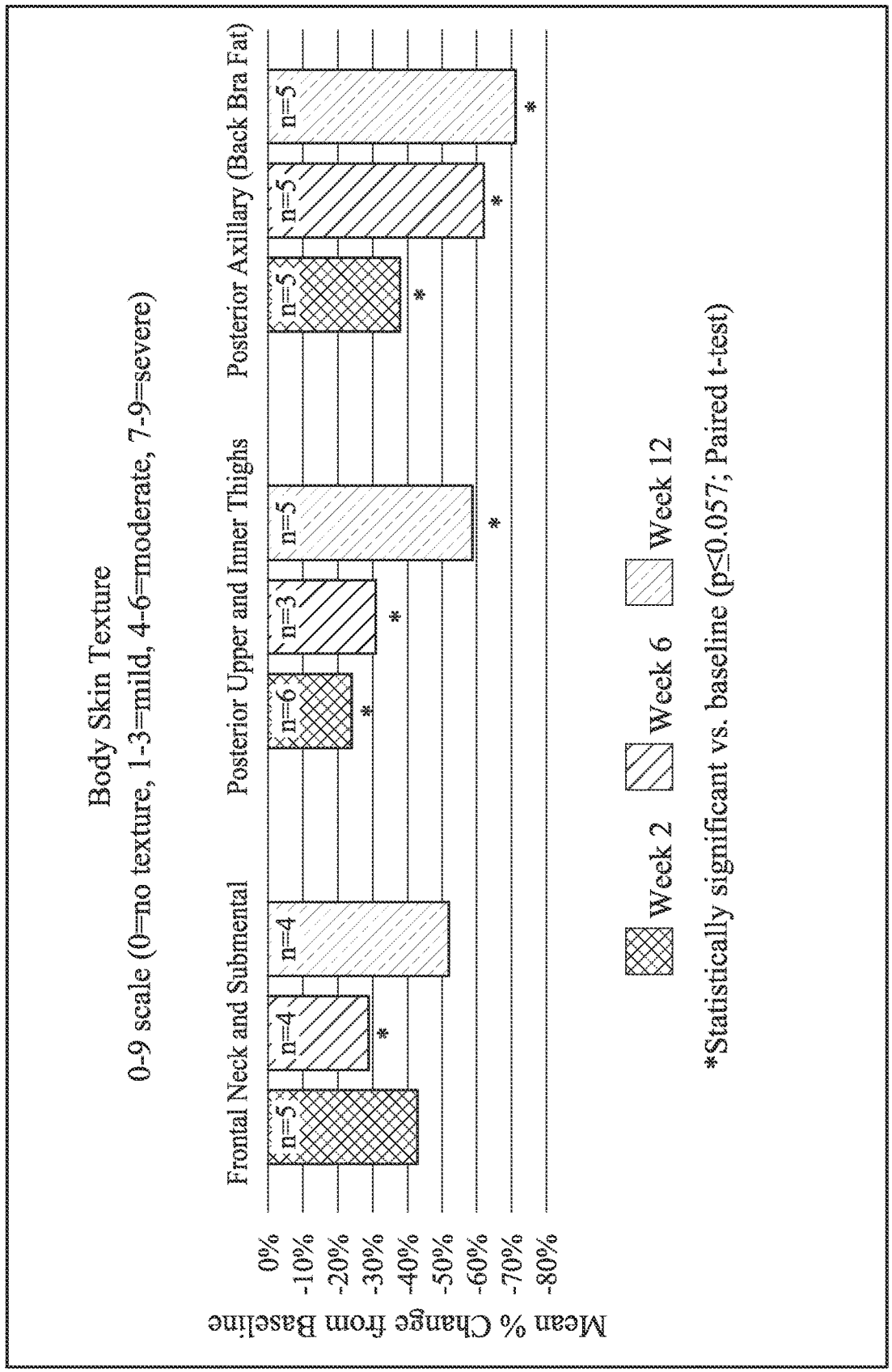
Figure 3E:
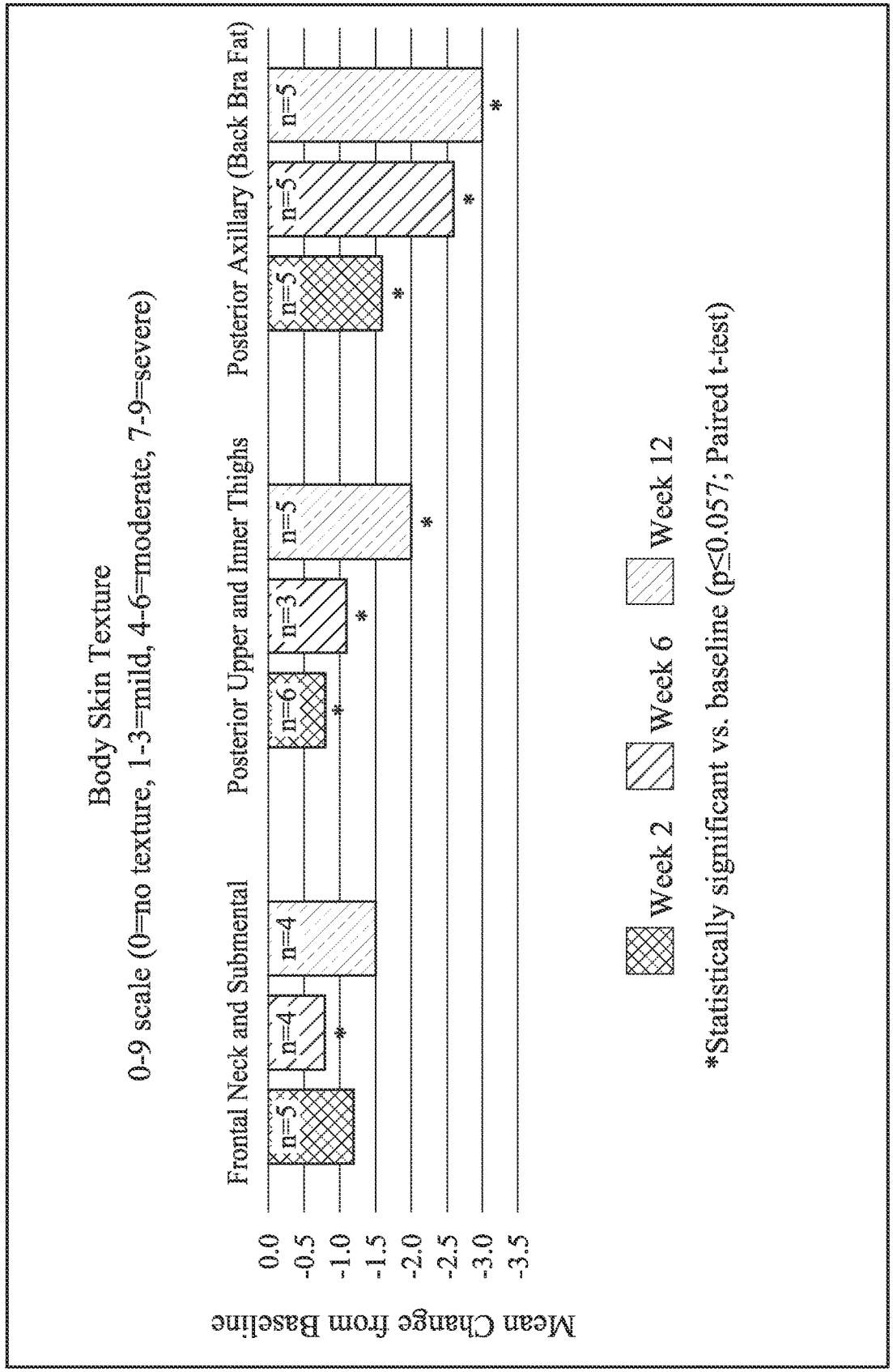
Figure 3F:
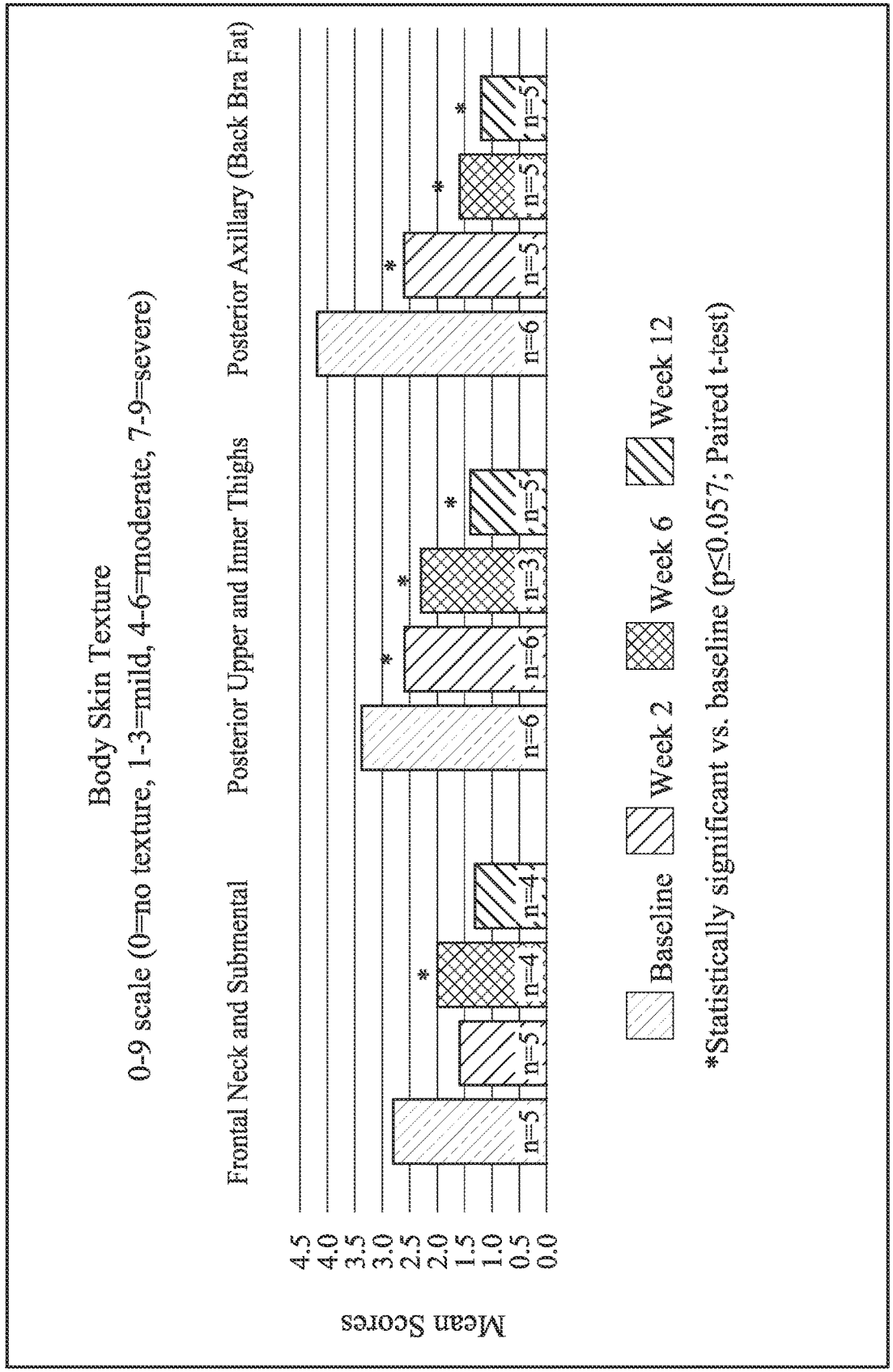
Figure 3G:
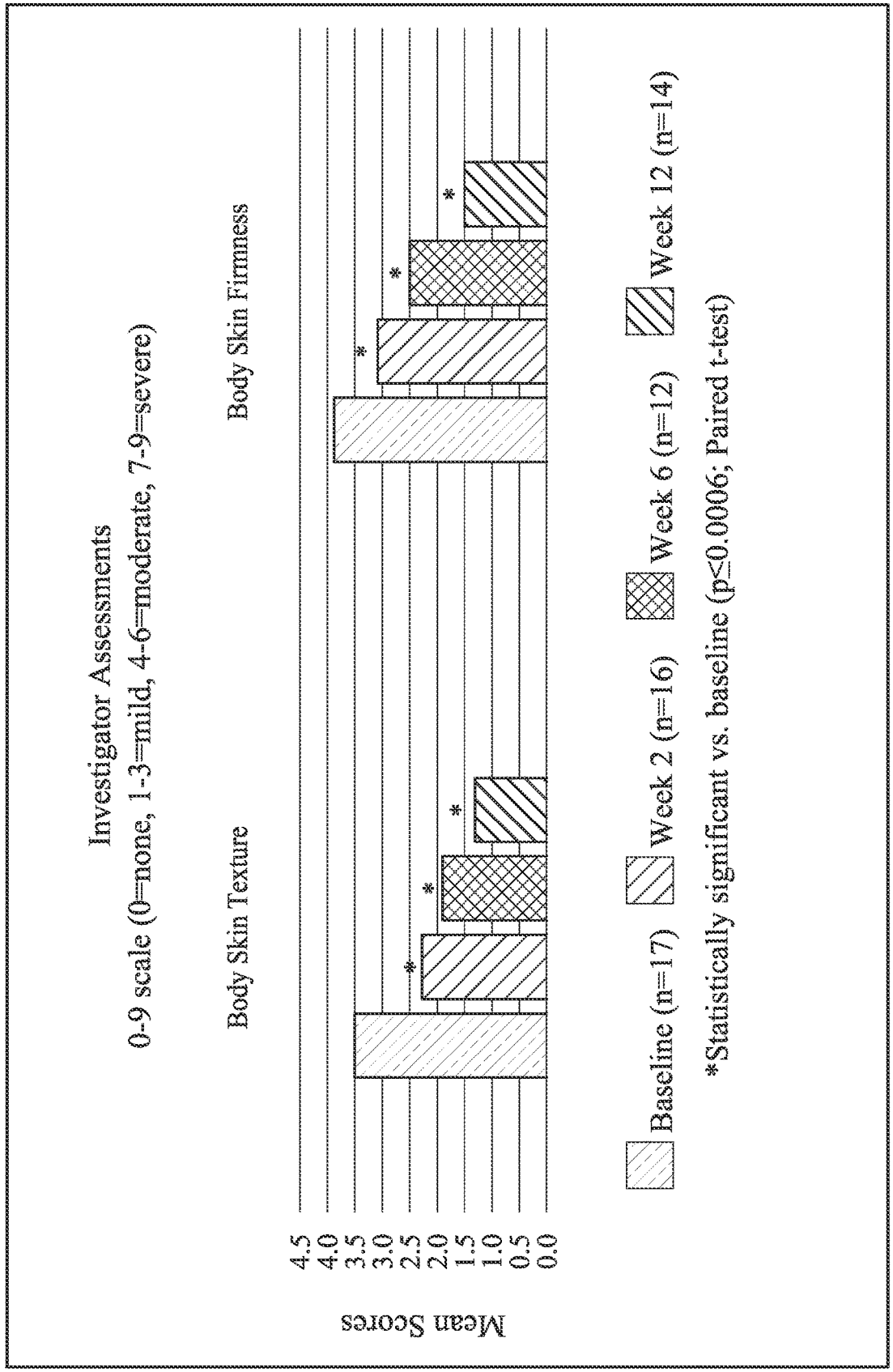

The results of the investigator assessments are also shown in FIGS. 3A to 3G wherein:

FIG. 3A shows the investigator assessment of the mean % change from baseline in body skin firmness per body area;

FIG. 3B shows the investigator assessment of the mean change from baseline in body skin firmness per body area;

FIG. 3C shows the investigator assessment of the mean scores in body skin firmness per body area;

FIG. 3D shows the investigator assessment of the mean % change from baseline in body skin texture per body area;

FIG. 3E shows the investigator assessment of the mean change from baseline in body skin texture per body area;

FIG. 3F shows the investigator assessment of the mean scores in body skin texture per body area; and FIG. 3G shows the investigator assessment of the mean scores in body skin texture and body skin firmness for all body areas.

The data reported in FIGS. 3A to 3G shows significant improvements compared to baseline for the investigator assessments on body skin firmness and body skin texture.

The data obtained from the subject self-assessment questionnaires showed:

By Week 2:
94% of subjects agreed that immediately after applying the topical composition, the subject's skin felt smooth and soft; and
94% of the subjects agreed that with continued use of the topical composition, the subject's skin felt hydrated.

By Week 6:
83% of subjects agreed that immediately after applying the topical composition, the subject's skin exhibited a reduction in roughness and dryness;
75% of subjects agreed that immediately after applying the topical composition, the subject's skin appeared smoother and firmer;
92% of the subjects agreed that with continued use of the topical composition, the subject's skin felt hydrated; and
75% of the subjects agreed that with continued use of the topical composition, the subject's skin exhibited improvements in overall appearance.

By Week 12:
100% of subjects agreed that immediately after applying the topical composition, the subject's skin felt smoother and softer;
93% of subjects agreed that immediately after applying the topical composition, the subject's skin felt hydrated;
79% of the subjects agreed that continued use of the topical composition: (i) helped enhance the effects of the body contouring procedure; (ii) helped the subject feel more confident about how their skin looked; (iii) helped maintain the appearance of the results achieved by the contouring procedure; and (iv) helped enhance the overall experience of the results achieved with the contouring procedure.

The invention illustratively described herein suitably may be practiced in the absence of any element or elements, limitation or limitations which is not specifically disclosed herein. Thus, for example, in each instance herein, any of the terms "comprising," "consisting essentially of" and "consisting of" may be replaced with either of the other two terms. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A method of improving the appearance of a subject's skin in a target area comprising applying twice a day to the skin of the target area, a topical composition comprising: (i) about 0.0001 wt % to about 2.00 wt % based on the total weight of the composition of one or more tripeptides, (ii) about 0.0001 wt % to about 2.00 wt % based on the total weight of the composition of one or more tetrapeptides (iii) one or more extracellular matrix ("ECM") botanical extract agents; (iv) one or more cellular recycling ("CR") botanical extract agents; (v) *Coleus forskohlii* root extract and one or more adipose targeting ("AT") botanical extract agents and (vi) *Zingiber officinale* (ginger) root extract and wherein the target area comprises abdominal, neck, chest, arm, leg, buttocks or combination thereof.

2. The method of claim 1 wherein the target area is a thigh region.

3. The method of claim 1 wherein the target area is an upper arm region.

4. The method of claim 1 wherein the composition comprises one or more ECM botanical extract agents selected from the groups consisting of *Chlorella vulgaris* extract, *Lentinus edodes* extract or a combination thereof.

5. The method of claim 1 wherein the composition comprises one or more CR botanical extract agents selected from the group consisting of *Melissa officinalis* leaf extract, rice extract or a combination thereof.

6. The method of claim 1 wherein the one or more AT botanical extract agents is selected from the group consisting of *Oenanthe javanica* extract, *Coffea arabica* (coffee) seed oil, *Brassica campestris* (rapeseed) sterols, *Coleus forskohlii* root extract, *Chlorella vulgaris/Lupinus albus* protein ferment and combinations thereof.

7. The method of claim 1 wherein the composition comprises one or more thickening agents.

8. The method of claim 7 wherein the one or more thickening agent comprises a polymer or copolymer with acryloyldimethyl taurate monomers.

9. The method of claim 1 wherein the composition comprises one or more film forming agents.

10. The method of claim 9 wherein the one or more film forming agents comprises a silicone containing compound.

11. The method of claim 1 wherein the composition comprises one or more $C_8$-$C_{24}$ alkanes.

12. The method of claim 11 wherein the one or more $C_8$-$C_{24}$ alkanes comprise a mixture of $C_{18}$-$C_{21}$ alkanes.

13. A method of improving the appearance of a subject's skin in a target area comprising applying twice a day to the skin of the target area, a topical composition comprising: (i) about 0.0001 wt % to about 2.00 wt % based on the total weight of the composition of one or more tripeptides; (ii) about 0.0001 wt % to about 2.00 wt % based on the total weight of the composition of one or more tetrapeptides; (iii) one or more extracellular matrix ("ECM") agents selected from the groups consisting of *Chlorella vulgaris* extract, *Lentinus edodes* extract or a combination thereof: (iv) one or more cellular recycling ("CR") agents selected from the group consisting of *Melissa officinalis* leaf extract, rice extract or a combination thereof; (v) *Coleus forskohlii* root extract and one or more adipose targeting ("AT") agents selected from the group consisting of *Oenanthe javanica* extract, *Coffea arabica* (coffee) seed oil, *Brassica campestris* (rapeseed) sterols, *Chlorella vulgaris/Lupinus albus* protein ferment and combinations thereof; (vi) *Zingiber officinale* (ginger) root extract; (vii) one or more thickening agents; (viii) one or more film forming agents; and (ix) one or more $C_8$-$C_{24}$ alkanes; and wherein the target area comprises abdominal, neck, chest, arm, leg, buttocks or combination thereof.

14. The method of claim 13 wherein the target area is a thigh region.

15. The method of claim 13 wherein the target area is an upper arm region.

16. The method of claim 13 wherein the composition is applied once in the morning and once in the evening for at least 6 weeks.

17. The method of claim 13 wherein the composition is applied once in the morning and once in the evening for at least 12 weeks.

18. The method of claim 13 wherein the one or more tripeptides has a VAL-TRY-VAL amino acid sequence and the one or more tetrapeptides has a LYS-ASP-VAL-TRY amino acid sequence.

19. A method of improving the appearance of a subject's skin in a target area comprising applying twice a day to the skin of the target area, a topical composition comprising:
  (i) about 0.0001 wt % to about 2.00 wt % based on the total weight of the composition of one or more tripeptides;
  (ii) about 0.0001 wt % to about 2.00 wt % based on the total weight of the composition of one or more tetrapeptides;
  (iii) *Chlorella vulgaris* extract;
  (iv) *Lentinus edodes* extract;
  (v) *Melissa officinalis* leaf extract;
  (vi) rice extract;
  (vii) *Oenanthe javanica* extract;
  (viii) *Coffea arabica* (coffee) seed oil,
  (ix) *Brassica campestris* (rapeseed) sterols,
  (x) *Coleus forskohlii* root extract;
  (xi) *Chlorella vulgaris/Lupinus albus* protein ferment;
  (xii) *Zingiber officinale* (ginger) root extract;
  (xiii) one or more thickening agents;
  (xiv) one or more film forming agents; and
  (xv) one or more $C_8$-$C_{24}$ alkanes;
  and wherein the target area comprises abdominal, neck, chest, arm, leg, buttocks or combination thereof.

20. The method of claim 19 wherein the one or more tripeptides has a VAL-TRY-VAL amino acid sequence and the one or more tetrapeptides has a LYS-ASP-VAL-TRY amino acid sequence.

* * * * *